(12) United States Patent
Langer et al.

(10) Patent No.: US 6,998,115 B2
(45) Date of Patent: *Feb. 14, 2006

(54) BIODEGRADABLE POLY(β-AMINO ESTERS) AND USES THEREOF

(75) Inventors: Robert S. Langer, Newton, MA (US); David M. Lynn, Somerville, MA (US); David Putnam, Cambridge, MA (US); Mansoor M. Amiji, Attleboro, MA (US); Daniel G. Anderson, Framingham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 427 days.

This patent is subject to a terminal disclaimer.

(21) Appl. No.: 09/969,431

(22) Filed: Oct. 2, 2001

(65) Prior Publication Data

US 2002/0131951 A1 Sep. 19, 2002

Related U.S. Application Data

(60) Provisional application No. 60/305,337, filed on Jul. 13, 2001, and provisional application No. 60/239,330, filed on Oct. 10, 2000.

(51) Int. Cl.
*A61K 31/765* (2006.01)
*C08G 69/44* (2006.01)
*C08G 63/44* (2006.01)
*C07C 327/00* (2006.01)

(52) U.S. Cl. .................... 424/78.37; 528/288; 528/362; 564/78

(58) Field of Classification Search .............. 424/783.7; 528/288, 362; 564/78; 544/162; 560/127; 548/335.5
See application file for complete search history.

(56) References Cited

U.S. PATENT DOCUMENTS 2,759,913 A   8/1956   Hulse ......................... 260/89.7
3,963,771 A   6/1976   Robson et al. .............. 260/482

(Continued)

FOREIGN PATENT DOCUMENTS

| DE | 25 20 814 | 11/1976 |
| DE | 196 26 567 | 1/1998 |
| WO | WO 98/16202 | 4/1998 |
| WO | WO 02/13767 | 2/2002 |

OTHER PUBLICATIONS

Angeloni et al. ("Liquid crystalline poly (beta–amino–ester) containing different mesogenic groups," in Makromolekulare Chemie (1985), 186(5), 977–997). Abstract.*

(Continued)

*Primary Examiner*—Thurman K. Page
*Assistant Examiner*—Blessing Fubara
(74) *Attorney, Agent, or Firm*—Brenda Herschbach Jarrell; C. Hunter Baker; Choate, Hall & Stewart

(57) ABSTRACT

Poly(β-amino esters) prepared from the conjugate addition of bis(secondary amines) or primary amines to a bis(acrylate ester) are described. Methods of preparing these polymers from commercially available starting materials are also provided. These tertiary amine-containing polymers are preferably biodegradable and biocompatible and may be used in a variety of drug delivery systems. Given the poly(amine) nature of these polymers, they are particularly suited for the delivery of polynucleotides. Nanoparticles containing polymer/polynucleotide complexes have been prepared. The inventive polymers may also be used to encapsulate other agents to be delivered. They are particularly useful in delivering labile agents given their ability to buffer the pH of their surroundings.

39 Claims, 7 Drawing Sheets

U.S. PATENT DOCUMENTS

| | | | |
|---|---|---|---|
| 5,180,424 A | 1/1993 | Hutter | 106/20 |
| 5,364,634 A | 11/1994 | Lew | 424/451 |
| 5,462,990 A | 10/1995 | Hubbell et al. | 525/54.1 |
| 5,858,746 A | 1/1999 | Hubbell et al. | 435/177 |
| 5,904,927 A | 5/1999 | Amiji | 424/422 |
| 5,962,520 A | 10/1999 | Smith et al. | 514/529 |
| 6,060,582 A | 5/2000 | Hubbell et al. | 528/354 |

OTHER PUBLICATIONS

Angeloni et al. ("Liquid crystalline poly (beta–amino ester) containing different mesogenic groups," in Makromolekulare Chemie (1985), 186(5), 977–997; cited in the last office action).*

Rao et al. (Poly (Butanediol Spermate): "A Hydrolytically Labile Polyester–Based Nitric Oxide Carrier," J. bioactive and Compatible Polymers 14: 54–63, 1999; provided by applicants on Form PTO 1449).*

Ferruti et al. ("Linear Amino Polymers: Synthesis, Protonation and Complex Formation," Advances in Polymer Science, 58:55–92, 1984; provided by applicants on Form PTO 1449).*

Ferruti et al. ("A Novel Modification of poly (L–lysine) Leading to a Soluble Cationic Polymer with Reduced toxicity and with Potential as a Transfection Agents," Macromol. Chem. Phyd. 199: 2565–2575, 1998; provided by applicants on Form PTO 1449).*

Akinc, et al., "Parallel Synthesis and Biophysical Characterization of Degradable Polymer Library of Gene Delivery", J. Am. Chem. Soc., 2003.

Akinc, et al., "Measuring the pH Environmental of DNA Delivered Using Nonviral Vectors: Implications of Lysosomal Trafficking", Biotechnol. Bioeng., 78(5): 503–508, 2002.

Barbucci, et al., "Macroinorganics. 7. Property–Stucture Relationships for Polymeric Bases Whose Monomeric Units Behave Independently toward Protonation" Macromolecules, 14: 1203–1209, 1981.

Barbucci, et al., "Protonation Studies of Multifunctional Polymers with a Poly(Amido–Amine) Stucture", Polymer, 19: 1329–1334, 1978.

Barbucci, et al., "Thermodynamic and $^{13}$C n.m.r. Data on the Protonation of Polymeric Bases Whose Repeating Units Behave Independently Towards Protonation" Polymer, 21: 81–85, 1980.

Benns, et al., "pH–Sensitive Cationic Polymer Gene Delivery Vehicle: N–Ac–Poly (L–Histidine)–Graft–Poly (L–Lysine) Comb Shaped Polyer", Bioconjugate Chem,. 11: 637–645, 2000.

Brocchini,"Combinatorial Chemistry and Biomedical Polymer Development" Advanced Drug Delivery Reviews, 53: 123–130, 2001.

Brocchini, et al., "A Combinatorial Approach for Polymer Design", Journal of the American Chemical Society, 119:4553–4554, 1997.

Caminschi, et al., "Molecular Cloning of F4/80–Like–Receptor, a Seven–Span Membrane Protein Expressed Differentially by Dendritic Cells and Monocyte–Macrophage Subpopulations", J. Immunol. 167: 3570–3576, 2001.

Capan, et al., "Preparation and Characterization of Poly (D, L–Lactide–Co–Glycolide) Microspheres for Controlled Release of Poly(L–Lysine) Complexed Plasmid DNA", Pharm. Res. 16: 509–513, 1999.

Casimiro, et al., "Vaccine–Induced Immunity in Baboons by Using DNA and Replication–Incompetent Adenovirus Type 5 Vectors Expressing a Human Immunodeficiency Virus Type 1 Gag Gene", J. Virol. 77: 7663–7668, 2003.

Cho, et al., "Homeotasis–Stimulated Proliferation Drives Naïve T Cells to Differentiate Directly into Memory T Cells", J. Exp. Med., 192: 549–556, 2000.

Cho, et al., "A Proposed Mechanism for the Induction of Cytotoxic T Lymphocyte Production by Heat Shock Fusion Proteins", Immunity, 12: 263–272, 2000.

Crooke, "Molecular Mechanisms of Action of Antisense Drugs" Biochim. Biophys. Acta, 1489(1): 31–44, 1999.

De Smedt, et al., Cationic Polymer Based Gene Delivery Systems, Pharmaceutical Research, 17(2): 113–126, 2000.

Ferruti, et al., "A Novel Modification of poly(L–lysine) Leading to a Soluble Cationic Polymer with Reduced Toxicity and with Potential as Transfection Agent", Macromol. Chem. Phys. 199: 2565–2575, 1998.

Fominaya, et al., "Target Cell–Specific DNA Transfer Mediated by a Chimeric Multidomain Protein", Journal of Biological Chemistry, 271(18): 10560–1996.

Fu, et al., "Visual Evidence of Acidic Environment within Degrading Poly(Lactic–Co–Glycolic Acid) (PLGA) Microspheres", Pharm. Res., 17: 100–106, 2000.

Garg, et al., "Genetic Tagging Shows Increased Frequency and Longevity of Antigen–Presenting, Skin–Derived Dendritic Cells in Vivo", Nature Immunology, 4: 907–912, 2003.

Gebhart, et al., "Evaluation of Polyplexes as Gene Transfer Agents" Journal of Controlled Release, 73: 401–416, 2001.

He, et al., "Experimental Investigation Into One–Step and Two–Steps Polymerization Via Michael Addition from Primary Amine", Polymer Preprints, 42(2): 335.

Hwang, et al., "Effects of Structure of β–Cyclodextrin–Containing Polymers on Gene Delivery", Bioconjugate Chem. 12: 280–290, 2001.

Lim, et al., "Biodegradable, Endosome Disruptive, and Cationic Network–Type Polymer as a Highly Efficient and Nontoxic Gene Delivery Carrier" Bioconjugate Chemistry, 13:952–957, 2002.

Lim, et al., "Cationic Hyperbranched Poly(Amino Ester): A Novel Class of DNA Condensing Molecule with Cationic Surface, Biodegradable Three–Dimensional Structure, and Tertiary Amine Groups in the Interior" J. Am. Chem. Soc. 123: 2460–2461, 2001.

Lim, et al., "Self–Assembled Ternary Complex of Cationic Dendrimer, Cucurbituril, and DNA", Noncovalent Strategy in Developing a Gene Delivery Carrier, Bioconjug Chem, 13(6): 1181–1185, 2002.

Loan, et al., "Poly(Amido–Amine)s and Poly(Ester–Amine)s based on Aromatic Amines Containing Carboxyl Groups", Macromolecular Chemistry and Physics, 11: 3525–3533, 1995.

Lynn, et al., "pH–Responsive Polymer Microspheres: Rapid Release of Encapsulated Material Within the Range of Intracellular Ph", Angew. Chem. Int. Ed. 40(9):1707–1710, 2001.

Lynn, et al., "Degradable Poly (β–Amino Esters): Synthesis Characterization, and Self–Assembly with Plasmid DNA", J. Am. Chem. Soc. 122:10761–10768, 2000.

Lynn, et al., "Accelerated Discovery of Synthetic Transfection Vectors: Parallel Synthesis ad Screening of a Degradable Polymer Library" J. Am Chem. Soc. 123:8155–8156, 2001.

Midoux, et al., "Efficient Gene Transfer by Histidylated Polylysine/pDNA Complexes", *Bioconjugate Chem.* 10: 406–411, 1999.

Murphy, et al., "A Combinatorial Approach to the Discovery of Efficient Cationic Peptoid Reagents for Gene Delivery" *Proc. Natl. Acad. Sci. USA,* 95: 1517–1522, 1998.

O'Hagan, et al., "Induction of Potent Immune Responses by Cationic Microparticles with Adsorbed Human Immnodeficiency Virus DNA Vaccines", *J. Virol.* 75: 9037–9043, 2001.

Putnam, et al., "Polymer–Based Gene Delivery with Low Cytotoxicity by a Unique Balance of Side–Chain Termini" *Proc. Natl. Acad. Sci, USA,* 98: 1200–1205, 2001.

Remy, et al., "Gene Transfer with Lipospermines and Polyethylenimines", *Advanced Drug Delivery Reviews,* 30:85–95, 1998.

Sahoo, et al., "Residual Polyvinyl Alcohol Associated with Poly(D,L–Lactide–Co–Glycolide) Nanoparticles Affects Their Physical Properties and Cellular Uptake", *J. Control Release,* 82: 105–114, 2002.

Shchori, Ehud, "Poly(Secondary Amine)s from Diacrylates and Diamines", *J. Polym. Sci. Polym,* 21:413–415, 1983.

Strong, et al., "A General Synthetic Route to Defined, Biologically Active Multivalent Arrays", *J. Am. Chem. Soc.* 121:6193–6196, 1999.

Wagner, et al., "Influenza Virus Hemagglutinin HA–2 N–Terminal Fusogenic Peptides Augment Gene Transfer by Transferrin–Polylysine–DNA Complexes: Toward a Synthetic Virus–Like Gene–Transfer Vehicle", *Proc. Natl Acad. Sci., USA,* 89(17): 7934–7938, 1992.

Walter, et al., "Microencapsulation of DNA Using Poly(DL-Lactide–Co–Glycolide): Stability Issues and Release Characteristics", *J. Control. Release,* 61: 361–374, 1999.

Wetering, et al., "Structure–Activity Relationships of Water-Soluble Cationic Methacrylate/Methacrylamide Polymers for Nonviral Gene Delivery", *Bioconjugate Chem.* 10:589–597, 1999.

Murphy, et al., "A Combinatorial Approach to the Discovery of Efficient Cationic Peptoid Reagents for Gene Delivery", *Proc. Natl Acad. Sci. USA,* 95:1517–1522, 1998.

Anderson, "Humen Gene Therapy" *Nature,* 392: 25–30, 1996.

Anderson, et al., "Biodegration and Biocompatibility of PLA and PLGA Microspheres" *Adv. Drug Delivery Rev.* 28: 5–24, 1997.

Ando, et al., "PLGA Microspheres Containing Plasmid DNA: Preservation of Supercoiled DNA via Cryopreparation and Carbohydrate Stabilization" *J. Pharm. Sci.* 88: 126–130, 1999.

Barrera, et al., "Synthesis and RGD Peptide Modification of a New Biodegradable Copolymer: Poly (lactic acid–co–lysine)" *J. Am. Chem. Soc.* 115:11010–11011, 1993.

Behr, "Synthetic Gene–Transfer Vectors" *Acc. Chem. Res.* 26: 274–278, 1993.

Behr, "The Proton Sponge: a Trick to Enter Cells the Viruses Did Not Expoit" *Chimia,* 51: 34–36, 1997.

Boussif, et al., "A Versatile Vector for Gene and Oligonucleotide Transfer into Cells in Culture and In Vivo: Polyethylenimine" *Proc. Natl. Acad. Sci. USA,* 92: 7297–7301, 1995.

Brazeau, et al., "In Vitro Myotoxicity of Selected Cationic Macromolecules Used Non–Viral Gene Delivery" *Pharm. Res.* 15: 680–684, 1998.

Choksakulnimitr et al., "In Vitro Cytotoxicity of Macromolecules in Different Cell Culture Systems" *Controlled Release,* 34: 233–241, 1995.

Cotten, et al., "Receptor–Mediated Transport of DNA into Eukaryotic Cells" *Methods Enzym.* 217: 618, 1993.

Crystal, "Transfer of Genes to Humans: Early Lessons and Obstacles to Success"*Science,* 270: 404–410, 1995.

Danusso, et al., "Synthesis of Tertiary Amine Polymers" *Polymer,* 11:88–113, 1970.

Demeneix, et al., In *Artificial Self–Assembling Systems for Gene Delivery* (Felgner, et al., Eds). American Chemical Society, Washington, D.C., 1996, 146–151.

Deshmukh, et al., "Liposome and Polylysine Mediated Gene Transfer" *New J. Chem.* 21: 113–124, 1997.

Ferruti, et al., "Linear Amino Polymers: Synthesis, Protonation and Complex Formation" *Advances in Polymer Science,* 58: 55–92, 1984.

Ferruti, et al., "Recent Results on Functional Polymers and Macromonomers of Interest as Biomaterials of for Biomaterial Modifcation" *Biomaterials,* 15: 1235–1241, 1994.

Ferruti, et al., "Synthesis, Characterisation and Antitumour Activity of Platinum (II) Complexes of Novel Functionalised Poly (Amido Amine)s" *Macromol. Chem. Phys.* 200: 1644–1654, 1999.

Ferruti, et al., "Synthesis, Physico–Chemical Properties and Biomedical Applications of Poly(amino–amine)s" *Polymer,* 26: 1336, 1985.

Fire, et al., "Potent and Specific Genetic Interference by Double–Stranded RNA in Caenorhabditis Elegans" *Nature,* 391: 806–811, 1998.

Friedman, "Human Gene Therapy—An Immature Genie,k But Certainly out of the Bottle" *Nature Med,* 2: 144–147, 1996.

Gerasimov, et al., "Cytosolic Drug Delivery Using pH– and Light–Sensitive Liposomes" *Adv. Drug Delivery Rev.* 38: 317–338, 1999.

Gonzalez, et al., "New Class of Polymers for the Delivery of Macromolecular Terapeutics" *Bioconjugate Chem.* 10: 1068–1074, 1999.

Haensler, et al., "Polyamidoamine Cascade Polymers Mediate Efficient Transfection of Cells In Culture" *Bioconjugate Chem.* 4:372–379, 1993.

Hanes, et al., "New Advances in Microsphere–Based Single–Dose Vaccines" *Adv. Drug Delivery Rev.* 28: 97–119, 1997.

Hanson, et al., "Re–Examination and Further Development of a Precise and Rapid Dye Method for Measuring Cell Growth/Cell Kill" *Immunol. Methods,* 119:203–210, 1989.

Hill, et al., "In Vitro Cytotoxicity of Poly(amidoamine)s: Relevance to DNA Delivery" *Biochim. Biophys. Acta,* 1427: 161–174, 1999.

Hope, et al., Cationic Lipids, Phosphatidylethanolamine and the Intracellular Delivery of Polymeric, Nucleic Acid–Based Drugs (Review), *Molecular Membrane Technology,* 15: 1–14, 1998.

Kabanov, et al., "DNA Complexes with Polycations for the Delivery of Genetic Material inot Cells" Bioconjugate Chem. 6:7–20, 1995.

Kargina, et al., "Self–Splitted Water–Soluble Ionogenic Polymers" *Vysokomol. Soedin. Seriya A,* 28: 1139–1144, 1986.

Kukowska–Latallo, et al., "Efficient Transfer of Genetic Material into Mammalian Cells Using Starburst Polyamindoamine Dendrimers" *Proc. Natl. Acad. Sci. USA,* 93: 4897–4902, 1996.

Kwon, et al., "Pseudopoly (Amino Acids): A Study of the Synthesis and Characterization of Poly(trans–4–hydroxy–N–acyl–L–proline esters)" *Macromolecules,* 22: 3250–3255, 1989.

Lim, et al., "A Self–Destroying Polycationic Polymer: Biodegradable Poly(4–Hydroxy–L–Proline Ester)" *J. Am. Chem. Soc.* 121: 5633–5639, 1999.

Lim, et al., "Development of a Safe Gene Delivery System Using Biodegradable Polymer, Poly [α–(4–Aminobutyl–L–Glycolic Acid]" *J. Am. Chem. Soc.* 122: 6524–6525, 2000.

Linhardt, et al., "Free–Radical Synthesis of Poly(2–Ethylacrylic Acid) Fractions of Low Polydispersity: Effects of Molecular Weight and Polydispersity on the pH–Dependent Conformational Transition in Aqueous Solution" *Macromolecules,* 32: 4457–4459, 1999.

Linhardt, et al., "pH–Induced Fusion and Lysis of PHosphatidylcholine Vesicles by Hydrophobic Polyelectrolyte Poly(2–ethylacrylic Acid)" *Langmuir,* 16: 122–127, 2000.

Luo, et al., "Synthetic DNA Delivery System" *Nat. Biotechnol.* 18: 33–37, 2000.

Mathiowitz, et al., "Polyanhydride Microspheres as Drug Carriers I. Hot–Melt Microencapsulation" *J. Controlled Release,* 5:13–22, 1987.

Mathiowitz, et al., "Polyanhydride Microspheres as Drug Carriers. II. Microencapsulation" *J. Appl. Polymer Sci.,* 35: 755–774, 1988.

Miller, "Cationic Liposomes for Gene Therapy" *Angew. Chem. Int. Ed.* 37: 1769–1785 1998.

Mulligan, "The Basic Science of Gene Therapy" *Science,* 260: 926–932, 1993.

O'Donnell, et al., "Preparation of Microspheres by the Solvent Evaporation Technique" *Adv. Drug. Delivery Rev.,* 28:25–42, 1997.

Okada, "One–and Three– Month Release Injectable Microspheres of the LH–RH Superagonist Leuproerlin Acetate" *Adv. Drug Delivery Rev.* 28: 43–70, 1997.

Putnam, et al., "Poly(4–hydroxy–L–proline ester): Low-Temperature Polycondensation and Plasmid" *Macromolecules* 32: 3658–3662, 1999.

Rao, et al., "Poly (Butaneodiol Spermate): A Hydrolytcally Labile Polyester–Based Nitric Oxide Carrier" *J. Bioactive and Compatible Polymers* 14: 54–63, 1999.

Roberts, et al., "Preliminary Biological Evaluation of Polyamidoamine (PAMAM) Starburst™ Dendrimers" *J. Biomed. Mater. Res.* 30: 53–65, 1996.

Sanford, "The Biolistic Process" Trends Biotechnol. 6:288–302, 1988.

Schaffer, et al., "Vector Unpacking as a Potential Barrier for Receptor–Mediated Polyplex Gene Delivery" *Biotechnol. Bioeng.*67: 598–606, 2000.

Schweikl, et al., "Triethylene Glycol Dimethacrylate Induces Large Deletions in the Hprt Gene of V79 Cells" *Mutat. Res.* 438: P71:P78, 1999.

Singh, et al., "Cationic Microparticles: A Potent Delivery System for DNA Vaccines" *Proc. Natl. Acad. Sci. USA,* 97: 811–816, 2000.

Tang, et al., "In Vitro Gene Delivery by Degraded Polyamidoamine Dendrimers" *Bioconjugate Chem.* 7:703–714, 1996.

Uhrich, "Hyperbranched Polymers for Drug Delivery" *Trends Polym. Sci.* 5: 388–393, 1997.

van de Wetering, et al., "Stucture–Activity Relationships of Water–Soluble Cationic Methacrylate/Methacrylamide Polymers for Nonviral Gene Delivery" *Bioconjugate Chem.* 10: 589–597, 1999.

Yang, et al., "A New Approach to Identifying Genotoxic Carcinogens: p53 Induction as an Indicator of Genotoxic Damage" *Carcinogenesis,* 19: P1117–P1125, 1998.

Zauner, et al., "Polylsine–Based Transfection Systems Utilizing Receptor–Mediated Delivery" *Adv. Drug. Del. Rev.* 30: 97–113, 1998.

Zhou, et al., "Preparation of Poly(L–serine ester): A Structural Analogue of Conventional Poly(L–serine)" *Macromolecules,* 23: 3399–3406, 1990.

\* cited by examiner

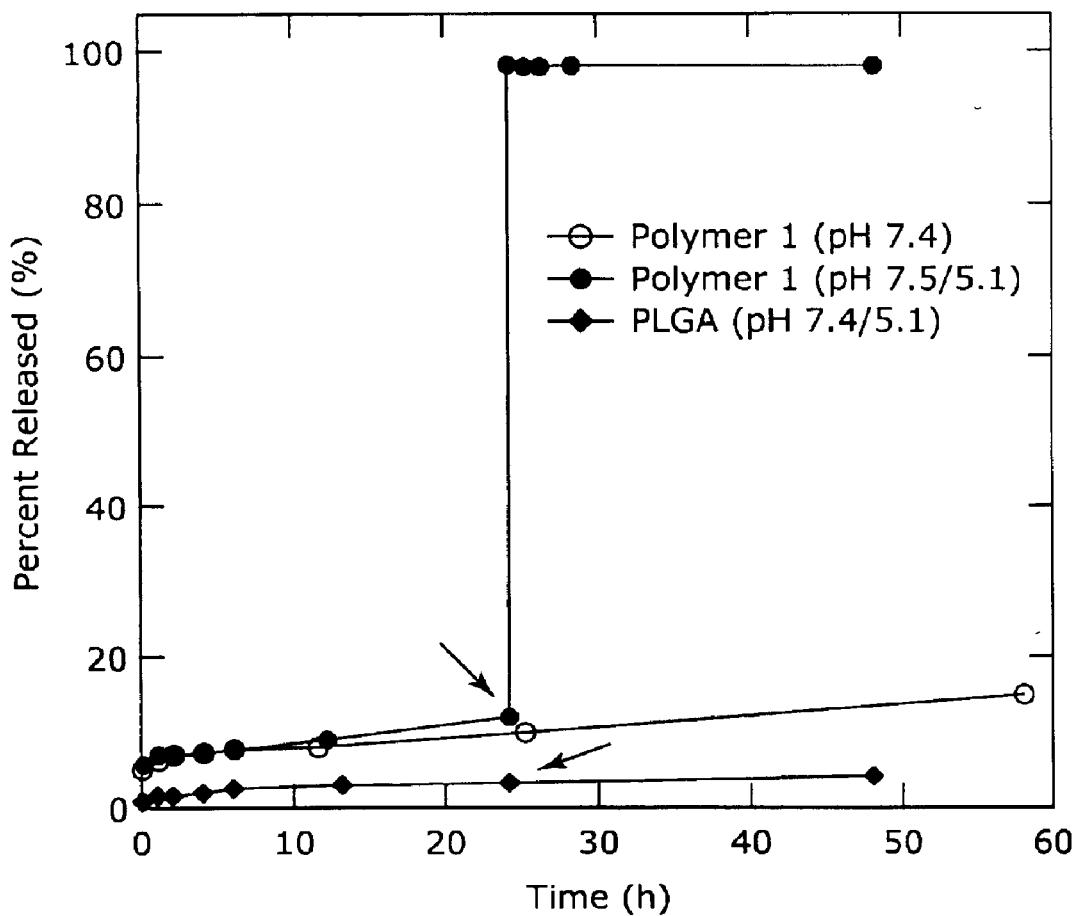
FIG. 7
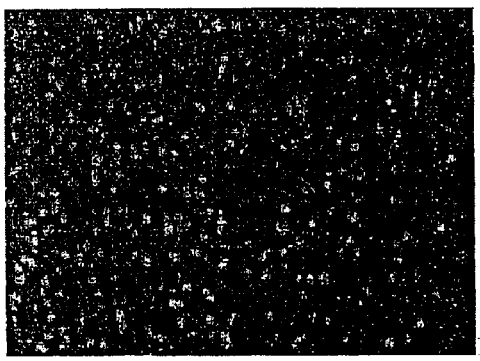 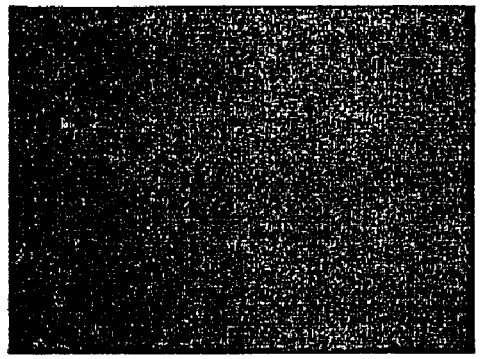
FIG. 8A          FIG. 8B

BIODEGRADABLE POLY(β-AMINO ESTERS) AND USES THEREOF

RELATED APPLICATIONS

The present application claims priority to co-pending provisional applications, U.S. Ser. No. 60/305,337, filed Jul. 13, 2001, and U.S. Ser. No. 60/239,330, filed Oct. 10, 2000, each of which is incorporated herein by reference.

GOVERNMENT SUPPORT

The work described herein was supported, in part, by grants from the National Science Foundation (Cooperative Agreement #ECC9843342 to the MIT Biotechnology Process Engineering Center), the National Institutes of Health (GM26698; NRSA Fellowship # 1 F32 GM20227-01), and the Department of the Army (Cooperative Agreement # DAMD 17-99-2-9-001 to the Center for Innovative Minimally Invasive Therapy). The United States government may have certain rights in the invention.

BACKGROUND OF THE INVENTION

The treatment of human diseases through the application of nucleotide-based drugs such as DNA and RNA has the potential to revolutionize the medical field (Anderson *Nature* 392(Suppl.):25–30, 1996; Friedman *Nature Med.* 2:144–147, 1996; Crystal *Science* 270:404–410, 1995; Mulligan *Science* 260:926–932, 1993; each of which is incorporated herein by reference). Thus far, the use of modified viruses as gene transfer vectors has generally represented the most clinically successful approach to gene therapy. While viral vectors are currently the most efficient gene transfer agents, concerns surrounding the overall safety of viral vectors, which include the potential for unsolicited immune responses, have resulted in parallel efforts to develop non-viral alternatives (for leading references, see: Luo et al. *Nat. Biotechnol.* 18:33–37,2000; Behr *Acc. Chem. Res.* 26:274–278, 1993; each of which is incorporated herein by reference). Current alternatives to viral vectors include polymeric delivery systems (Zauner et al. *Adv. Drug Del. Rev.* 30:97–113, 1998; Kabanov et al. *Bioconjugate Chem.* 6:7–20, 1995; each of which is incorporated herein by reference), liposomal formulations (Miller *Angew. Chem. Int. Ed.* 37:1768–1785, 1998; Hope et al. *Molecular Membrane Technology* 15:1–14, 1998; Deshmukh et al. *New J. Chem.* 21:113–124, 1997; each of which is incorporated herein by reference), and "naked" DNA injection protocols (Sanford *Trends Biotechnol.* 6:288–302, 1988; incorporated herein by reference). While these strategies have yet to achieve the clinical effectiveness of viral vectors, the potential safety, processing, and economic benefits offered by these methods (Anderson *Nature* 392(Suppl.):25–30, 1996; incorporated herein by reference) have ignited interest in the continued development of non-viral approaches to gene therapy (Boussif et al. *Proc. Natl. Acad. Sci. USA* 92:7297–7301, 1995; Putnam et al. *Macromolecules* 32:3658–3662, 1999; Lim et al. *J. Am. Chem. Soc.* 121:5633–5639, 1999; Gonzalez et al. *Bioconjugate Chem.* 10: 1068–1074, 1999; Kukowska-Latallo et al. *Proc. Natl. Acad. Sci. USA* 93:4897–4902, 1996; Tang et al. *Bioconjugate Chem.* 7:703–714, 1996; Haensler et al. *Bioconjugate Chem.* 4:372–379, 1993; each of which is incorporated herein by reference).

Cationic polymers have been widely used as transfection vectors due to the facility with which they condense and protect negatively charged strands of DNA. Amine-containing polymers such as poly(lysine) (Zauner et al. *Adv. Drug Del. Rev.* 30:97–113, 1998; Kabanov et al. *Bioconjugate Chem.* 6:7–20, 1995; each of which is incorporated herein by reference), poly(ethylene imine) (PEI) (Boussif et al. *Proc. Natl. Acad. Sci. USA* 92:7297–7301, 1995; incorporated herein by reference), and poly(amidoamine) dendrimers (Kukowska-Latallo et al. *Proc. Natl. Acad. Sci. USA* 93:4897–4902, 1996; Tang et al. *Bioconjugate Chem.* 7:703–714, 1996; Haensler et al. *Bioconjugate Chem.* 4:372–379, 1993; each of which is incorporated herein by reference) are positively-charged at physiological pH, form ion pairs with nucleic acids, and mediate transfection in a variety of cell lines. Despite their common use, however, cationic polymers such as poly(lysine) and PEI can be significantly cytotoxic (Zauner et al. *Adv. Drug Del. Rev.* 30:97–113, 1998; Deshmukh et al. *New J. Chem.* 21:113–124, 1997; Choksakulnimitr et al. *Controlled Release* 34:233–241, 1995; Brazeau et al. *Pharm. Res.* 15:680–684, 1998; each of which is incorporated herein by reference). As a result, the choice of cationic polymer for a gene transfer application generally requires a trade-off between transfection efficiency and short- and long-term cytotoxicity. Additionally, the long-term biocompatibility of these polymers remains an important issue for use in therapeutic applications in vivo, since several of these polymers are not readily biodegradable (Uhrich *Trends Polym. Sci.* 5:388–393, 1997; Roberts et al. *J. Biomed. Mater. Res.* 30:53–65, 1996; each of which is incorporated herein by reference).

In order to develop safe alternatives to existing polymeric vectors and other functionalized biomaterials, degradable polyesters bearing cationic side chains have been developed (Putnam et al. *Macromolecules* 32:3658–3662, 1999; Barrera et al. *J. Am. Chem. Soc.* 115:11010–11011, 1993; Kwon et al. *Macromolecules* 22:3250–3255, 1989; Lim et al. *J. Am. Chem. Soc.* 121:5633–5639, 1999; Zhou et al. *Macromolecules* 23:3399–3406, 1990; each of which is incorporated herein by reference). Examples of these polyesters include poly(L-lactide-co-L-lysine) (Barrera et al. *J. Am. Chem. Soc.* 115:11010–11011, 1993; incorporated herein by reference), poly(serine ester) (Zhou et al. *Macromolecules* 23:3399–3406, 1990; each of which is incorporated herein by reference), poly(4-hydroxy-L-proline ester) (Putnam et al. *Macromolecules* 32:3658–3662, 1999.; Lim et al. *J. Am. Chem. Soc.* 121:5633–5639, 1999; each of which is incorporated herein by reference), and more recently, poly[α-(4-aminobutyl)-L-glycolic acid]. Poly(4-hydroxy-L-proline ester) and poly[α-(4-aminobutyl)-L-glycolic acid] were recently demonstrated to condense plasmid DNA through electrostatic interactions, and to mediate gene transfer (Putnam et al. *Macromolecules* 32:3658–3662, 1999; Lim et al. *J. Am. Chem. Soc.* 121:5633–5639, 1999; each of which is incorporated herein by reference). Importantly, these new polymers are significantly less toxic than poly(lysine) and PEI, and they degrade into non-toxic metabolites. It is clear from these investigations that the rational design of amine-containing polyesters can be a productive route to the development of safe, effective transfection vectors. Unfortunately, however, present syntheses of these polymers require either the independent preparation of specialized monomers (Barrera et al. *J. Am. Chem. Soc.* 115:11010–11011, 1993; incorporated herein by reference), or the use of stoichiometric amounts of expensive coupling reagents (Putnam et al. *Macromolecules* 32:3658–3662, 1999; incorporated herein by reference). Additionally, the amine functionalities in the monomers must be protected prior to polymerization (Putnam et al *Macromolecules* 32:3658–3662, 1999; Lim et al. *J. Am. Chem. Soc.*

121:5633–5639, 1999; Gonzalez et al. *Bioconjugate Chem.* 10:1068–1074, 1999; Barrera et al. *J. Am. Chem. Soc.* 115:11010–11011, 1993; Kwon et al. *Macromolecules* 22:3250–3255, 1989; each of which is incorporated herein by reference), necessitating additional post-polymerization deprotection steps before the polymers can be used as transfection agents.

There exists a continuing need for non-toxic, biodegradable, biocompatible polymers that can be used to transfect nucleic acids and that are easily prepared efficiently and economically. Such polymers would have several uses, including the delivery of nucleic acids in gene therapy as well as in the packaging and/or delivery of diagnostic, therapeutic, and prophylactic agents.

SUMMARY OF THE INVENTION

The present invention provides polymers useful in preparing drug delivery devices and pharmaceutical compositions thereof. The invention also provides methods of preparing the polymers and methods of preparing microspheres and other pharmaceutical compositions containing the inventive polymers.

The polymers of the present invention are poly(β-amino esters) and salts thereof. Preferred polymers are biodegradable and biocompatible. Typically, the polymers have one or more tertiary amines in the backbone of the polymer. Preferred polymer have one or two tertiary amines per repeating backbone unit. The polymers may also be co-polymers in which one of the components is a poly(β-amino ester). The polymers of the invention may readily be prepared by condensing bis(secondary amines) or primary amines with bis(acrylate esters). A typical polymer of the invention is represented by the formulas below:

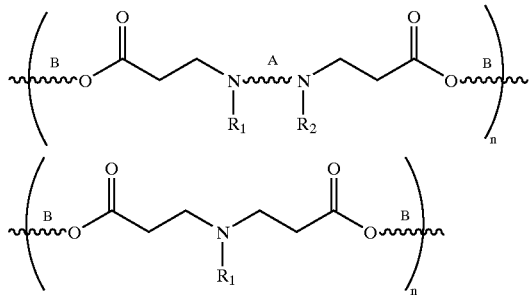

where A and B are linkers which may be any substituted or unsubstituted, branched or unbranched chain of carbon atoms or heteroatoms. The groups $R_1$ and $R_2$ may be any of a wide variety of substituents. In a particularly preferred embodiment, the groups $R_1$ and/or $R_2$ form cyclic structures with the linker A (please see the Detailed Description section below). Polymers containing such cyclic moieties have the characteristic of being more soluble at lower pH. Specifically preferred polymers are those that are insoluble in aqueous solutions at physiologic pH (pH 7.2–7.4) and are soluble in aqueous solutions below physiologic pH (pH<7.2). Other preferred polymers are those that are soluble in aqueous solution at physiologic pH (pH 7.2–7.4) and below.

In another aspect, the present invention provides a method of preparing the inventive polymers. In a preferred embodiment, commercially available or readily available monomers, bis(secondary amines), primary amines, and bis(acrylate esters), are subjected to conditions which lead to the conjugate addition of the amine to the bis(acrylate ester).

In a particularly preferred embodiment, each of the monomers is dissolved in an organic solvent (e.g., THF, diethyl ether, methylene chloride, hexanes, etc.), and the resulting solutions are combined and heated for a time sufficient to lead to polymerization of the monomers. The resulting polymer may then be purified using techniques known in the art.

In yet another aspect of the invention, the polymers are used to form nanometer-scale complexes with nucleic acids. The polynucleotide/polymer complexes may be formed by adding a solution of polynucleotide to a vortexing solution of the polymer at a desired DNA/polymer concentration. The weight to weight ratio of polynucleotide to polymer may range from 1:0.1 to 1:50, preferably from 1:1 to 1:20, more preferably from 1:1 to 1:10. The cationic polymers condense the polynucleotide into soluble particles typically 50–500 nm in size. These polynucleotide/polymer complexes may be used in the delivery of polynucleotides to cells. In a particularly preferred embodiment, these complexes are combined with pharmaceutical excipients to form pharmaceutical compositions suitable for delivery to animals including humans.

In another aspect of the invention, the polymers are used to encapsulate therapeutic, diagnostic, and/or prophylactic agents including polynucleotides to form microparticles. Typically these microparticles are an order of magnitude larger than the polynucleotide/polymer complexes. The microparticles range from 1 micrometer to 500 micrometers. In a particularly preferred embodiment, these microparticles allow for the delivery of labile small molecules, proteins, peptides, and/or polynucleotides to an individual. The microparticles may be prepared using any of the techniques known in the art to make microparticles, such as, for example, double emulsion and spray drying. In a particularly preferred embodiment, the microparticles can be used for pH-triggered delivery of the encapsulated contents due to the pH-responsive nature of the polymers (i. e., being more soluble at lower pH).

Definitions

The following are chemical terms used in the specification and claims:

The term alkyl as used herein refers to saturated, straight- or branched-chain hydrocarbon radicals derived from a hydrocarbon moiety containing between one and twenty carbon atoms by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term alkoxy as used herein refers to an alkyl groups, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy.

The term alkenyl denotes a monovalent group derived from a hydrocarbon moiety having at least one carbon-carbon double bond by the removal of a single hydrogen atom. Alkenyl groups include, for example, ethenyl, propenyl, butenyl, 1-methyl-2-buten-1-yl, and the like.

The term alkynyl as used herein refers to a monovalent group derived form a hydrocarbon having at least one carbon-carbon triple bond by the removal of a single hydrogen atom. Representative alkynyl groups include ethynyl, 2-propynyl (propargyl), 1-propynyl, and the like.

The term alkylamino, dialkylamino, and trialkylamino as used herein refers to one, two, or three, respectively, alkyl groups, as previously defined, attached to the parent molecular moiety through a nitrogen atom. The term alkylamino refers to a group having the structure—NHR' wherein R' is an alkyl group, as previously defined; and the term dialkylamino refers to a group having the structure—NR'R", wherein R' and R" are each independently selected from the group consisting of alkyl groups. The term trialkylamino refers to a group having the structure—NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Example include, but are not limited to, methylamino, dimethylamino, ethylamino, diethylamino, diethylaminocarbonyl, methylethylamino, isopropylamino, piperidino, trimethylamino, and propylamino.

The terms alkylthioether and thioalkoxy refer to an alkyl group, as previously defined, attached to the parent molecular moiety through a sulfur atom.

The term aryl as used herein refers to carbocyclic ring system having at least one aromatic ring including, but not limited to, phenyl, naphthyl, tetrahydronaphthyl, indanyl, indenyl, and the like. Aryl groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. In addition, substituted aryl groups include tetrafluorophenyl and pentafluorophenyl.

The term carboxylic acid as used herein refers to a group of formula —CO$_2$H.

The terms halo and halogen as used herein refer to an atom selected from fluorine, chlorine, bromine, and iodine.

The term heterocyclic, as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl) piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl) piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl) piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl) piperazine, 4-(2-nitrophenyl)piperazine, 4-(2-phenylethyl) piperazine, 4-(2-pyridyl)piperazine, 4-(2-pyrimidinyl) piperazine, 4-(2,3-dimethylphenyl)piperazine, 4-(2,4-difluorophenyl) piperazine, 4-(2,4-dimethoxyphenyl) piperazine, 4-(2,4-dimethylphenyl)piperazine, 4-(2,5-dimethylphenyl)piperazine, 4-(2,6-dimethylphenyl) piperazine, 4-(3-chlorophenyl)piperazine, 4-(3-methylphenyl)piperazine, 4-(3-trifluoromethylphenyl) piperazine, 4-(3,4-dichlorophenyl)piperazine, 4-3,4-dimethoxyphenyl)piperazine, 4-(3,4-dimethylphenyl) piperazine, 4-(3,4-methylenedioxyphenyl)piperazine, 4-(3, 4,5-trimethoxyphenyl)piperazine, 4-(3,5-dichlorophenyl) piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term carbamoyl, as used herein, refers to an amide group of the formula —CONH$_2$.

The term carbonyldioxyl, as used herein, refers to a carbonate group of the formula —O—CO—OR.

The term hydrocarbon, as used herein, refers to any chemical group comprising hydrogen and carbon. The hydrocarbon may be substituted or unsubstitued. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g, an aryl group substituent may have another substituent off it, such as another aryl group, which is further substituted with fluorine at one or more positions).

The term thiohydroxyl, as used herein, refers to a thiol of the formula —SH.

The term ureido, as used herein, refers to a urea groups of the formula —NH—CO—NH$_2$.

The following are more general terms used throughout the present application:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

BRIEF DESCRIPTION OF THE DRAWING

FIG. 7 shows the release profiles of rhodamine/dextran from polymer 1 and PLGA microspheres at various pH values. The arrows indicate the points at which HEPES buffer (pH 7.4) was exchanged with acetate buffer (pH 5.1).

FIG. 8A shows a representative fluorescence microscopy image of rhodamine/dextran-loaded polymer 1 microspheres suspended in HEPES buffer (pH 7.4). FIG. 8*b* shows a sample of loaded polymer 1 microspheres at pH 7.4 after addition of acetate buffer (pH 5.1). The direction of diffusion of acid is from the top right to the bottom left of the image (elapsed time≈5 seconds).

DETAILED DESCRIPTION OF CERTAIN PREFERRED EMBODIMENTS OF THE INVENTION

Figure 1:
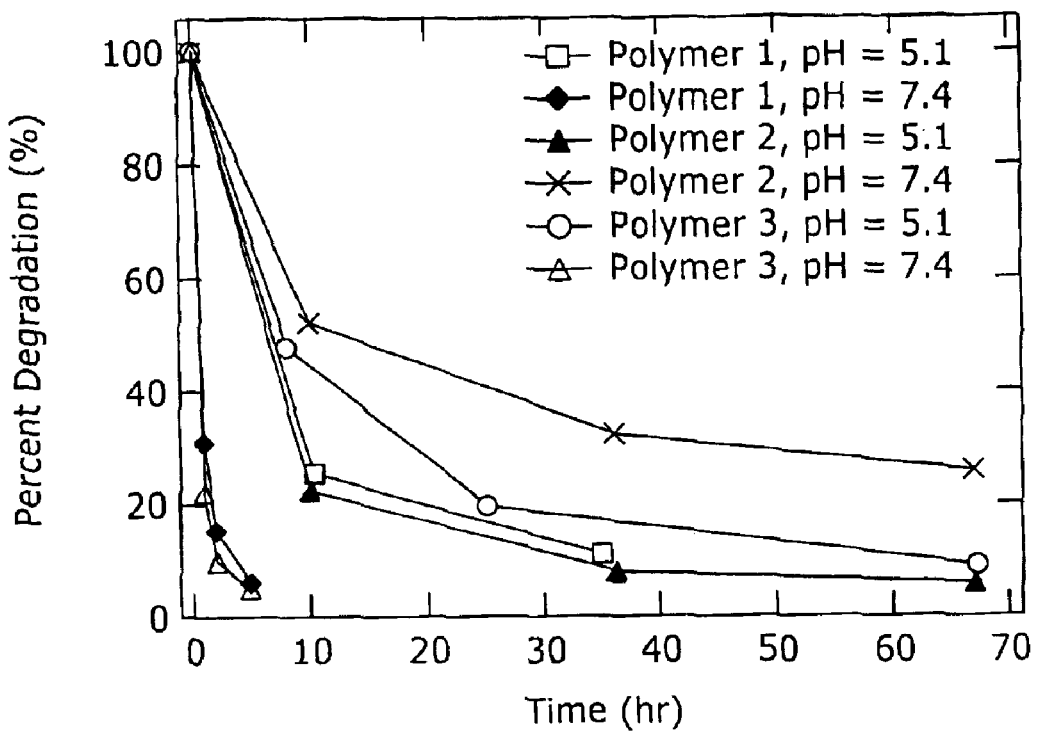
FIG. 1 shows the time profile for the degradation of polymers 1–3 at 37° C. at pH 5.1 and pH 7.4. Degradation is expressed as percent degradation over time based on GPC data.

The present invention provides improved polymeric encapusulation and delivery systems based on the use of β-amino ester polymers. The sytems may be used in the pharmaceutical/drug delivery arts to delivery polynucleotides, proteins, small molecules, peptides, antigen, drugs, etc. to a patient, tissue, organ, cell, etc.

The β-amino ester polymers of the present invention provide for several different uses in the drug delivery art. The polymers with their tertiary amine-containing backbones may be used to complex polynucleotides and thereby enhance the delivery of polynucleotide and prevent their degradation. The polymers may also be used in the formation of nanoparticles or microparticles containing encapsulated agents. Due to the polymers' properties of being biocompatible and biodegradable, these formed particles are also biodegradable and biocompatible and may be used to provide controlled, sustained release of the encapsulated agent. These particles may also be responsive to pH changes given the fact that these polymers are typically not substantially soluble in aqueous solution at physiologic pH but are more soluble at lower pH.

Polymers

The polymers of the present invention are poly(β-amino esters) containing tertiary amines in their backbones and salts thereof. The molecular weights of the inventive polymers may range from 5,000 g/mol to over 100,000 g/mol, more preferably from 4,000 g/mol to 50,000 g/mol. In a particularly preferred embodiment, the inventive polymers are relatively non-cytotoxic. In another particularly preferred embodiment, the inventive polymers are biocompatible and biodegradable. In a particularly preferred embodiment, the polymers of the present invention have $pK_a$s in the range of 5.5 to 7.5, more preferably between 6.0 and 7.0. In another particularly preferred embodiment, the polymer may be designed to have a desired $pK_a$ between 3.0 and 9.0, more preferably between 5.0 and 8.0. The inventive polymers are particularly attractive for drug delivery for several reasons: 1) they contain amino groups for interacting with DNA and other negatively charged agents, for buffering the pH, for causing endosomolysis, etc.; 2) they contain degradable polyester linkages; 3) they can be synthesized from commercially available starting materials; and 4) they are pH responsive and future generations could be engineered with a desired $pK_a$.

The polymers of the present invention can generally be defined by the formula (I):

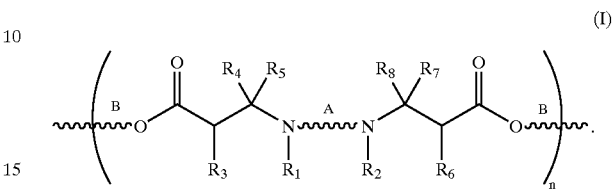

(I)

The linkers A and B are each a chain of atoms covalently linking the amino groups and ester groups, respectively. These linkers may contain carbon atoms or heteroatoms (e.g., nitrogen, oxygen, sulfur, etc.). Typically, these linkers are 1 to 30 atoms long, more preferably 1–15 atoms long. The linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. The groups $R_1$, $R_2$, $R_3$, $R_4$, $R_5$, $R_6$, $R_7$, and $R_8$ may be any chemical groups including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido groups. In the inventive polymers, n is an integer ranging from 5 to 10,000, more preferably from 10 to 500.

In a particularly preferred embodiment, the bis(secondary amine) is a cyclic structure, and the polymer is generally represented by the formula II:

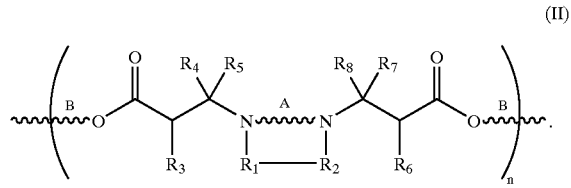

(II)

In this embodiment, $R_1$ and $R_2$ are directly linked together as shown in formula II. Examples of inventive polymers in this embodiment include, but are not limited to formulas III and IV:

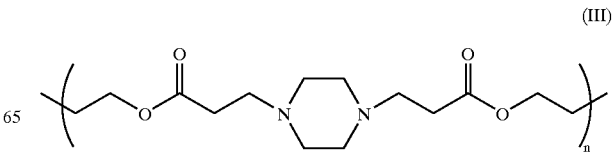

(III)

(IV)

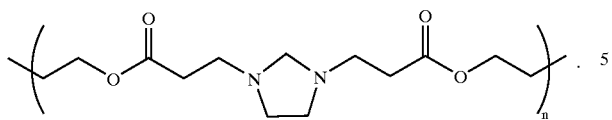

As described above in the preceding paragraph, any chemical group that satisfies the valency of each atom may be substituted for any hydrogen atom.

In another particularly preferred embodiment, the groups $R_1$ and/or $R_2$ are covalently bonded to linker A to form one or two cyclic structures. The polymers of the present embodiment are generally represented by the formula V in which both $R_1$ and $R_2$ are bonded to linker A to form two cyclic structures:

(V)

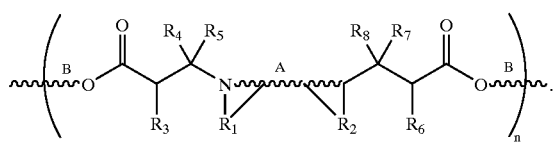

The cyclic structures may be 3-, 4-, 5-, 6-, 7-, or 8-membered rings or larger. The rings may contain heteroatoms and be unsaturated. Examples of polymers of formula V include formulas VI, VII, and VIII:

(VI)

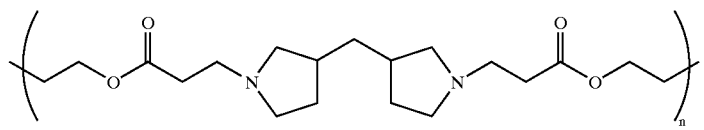

(VII)

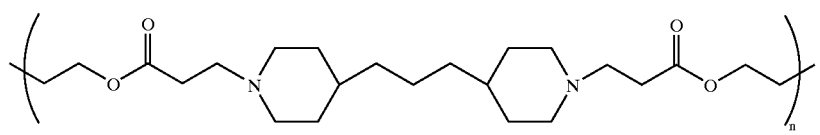

(VIII)

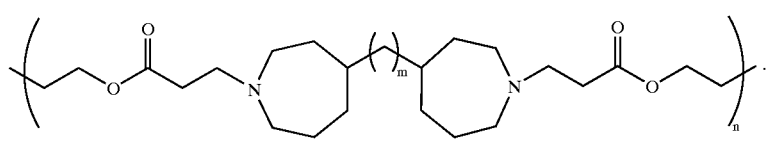

As described above, any chemical group that satisfies the valency of each atom in the molecule may be substituted for any hydrogen atom.

In another embodiment, the polymers of the present invention can generally be defined by the formula (IX):

(IX)

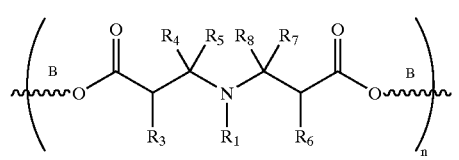

The linker B is a chain of atoms covalently linking the ester groups. The linker may contain carbon atoms or heteroatoms (e.g., nitrogen, oxygen, sulfur, etc.). Typically, the linker is 1 to 30 atoms long, more preferably 1–15 atoms long. The linker may be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. Each of R1, R3, R4, R5, R6, R7, and R8 may be independently any chemical group including, but not limited to, hydrogen atom, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido groups. In the inventive polymer, n is an integer ranging from 5 to 10,000, more preferably from 10 to 500.

In another embodiment, the bis(acrylate ester) unit in the inventive polymer is chosen from the following group of bis(acrylate ester) units (A–G):

A

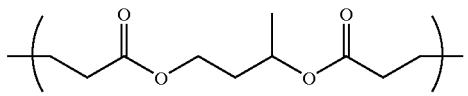

-continued

B

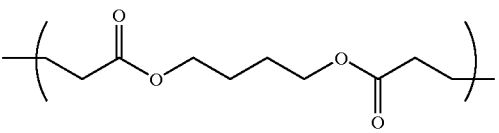

C

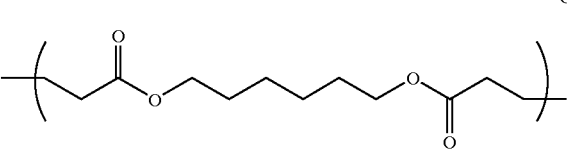

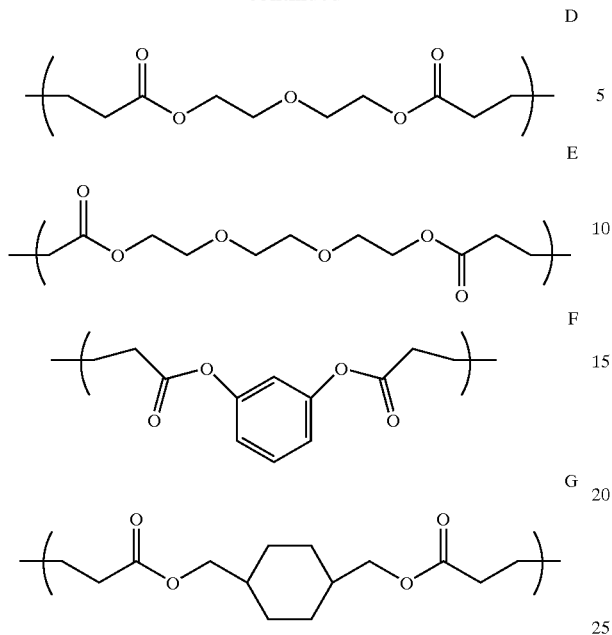
In certain embodiments, the polymer comprises the bis(acrylate ester) G.
In another embodiment, the amine in the inventive polymer is chosen from the following group of amines (1–20):
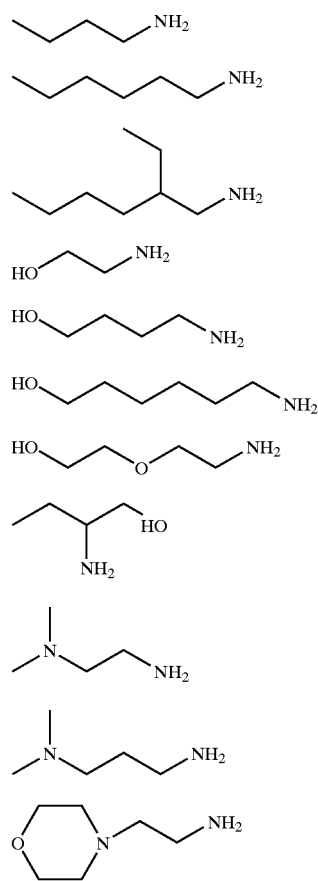
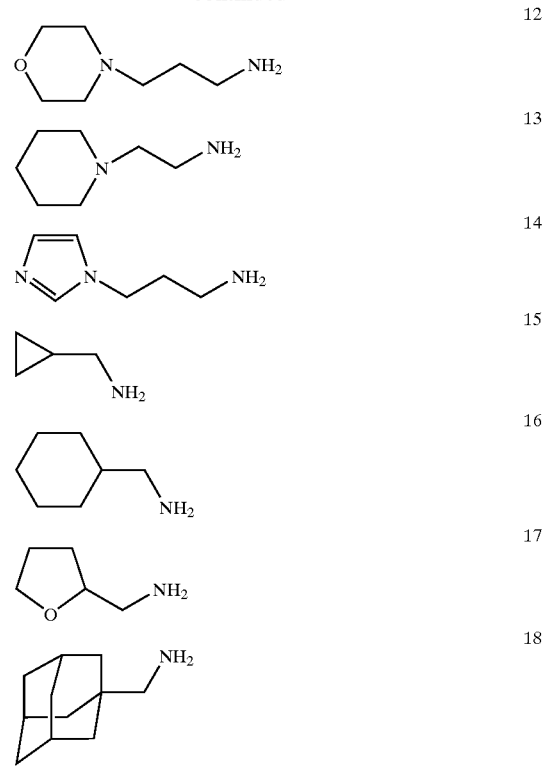
In certain embodiments, the polymer comprises the amine 5. In other embodiments, the polymer comprises amine 14.
Particular examples of the polymers of the present invention include:
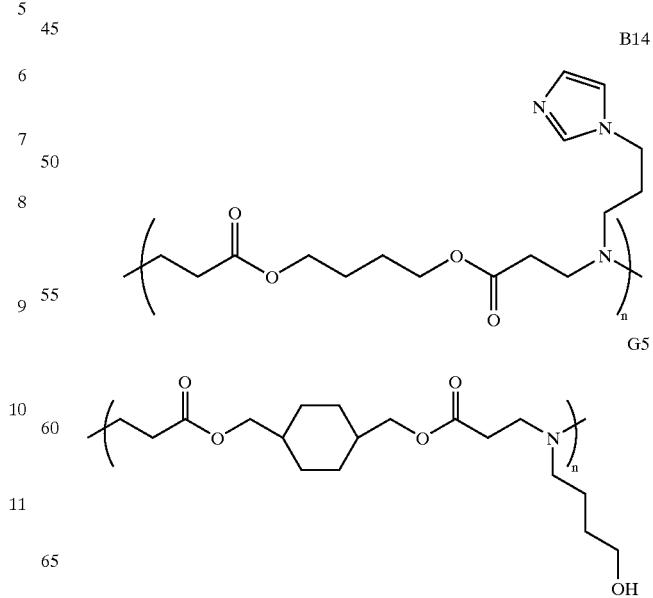

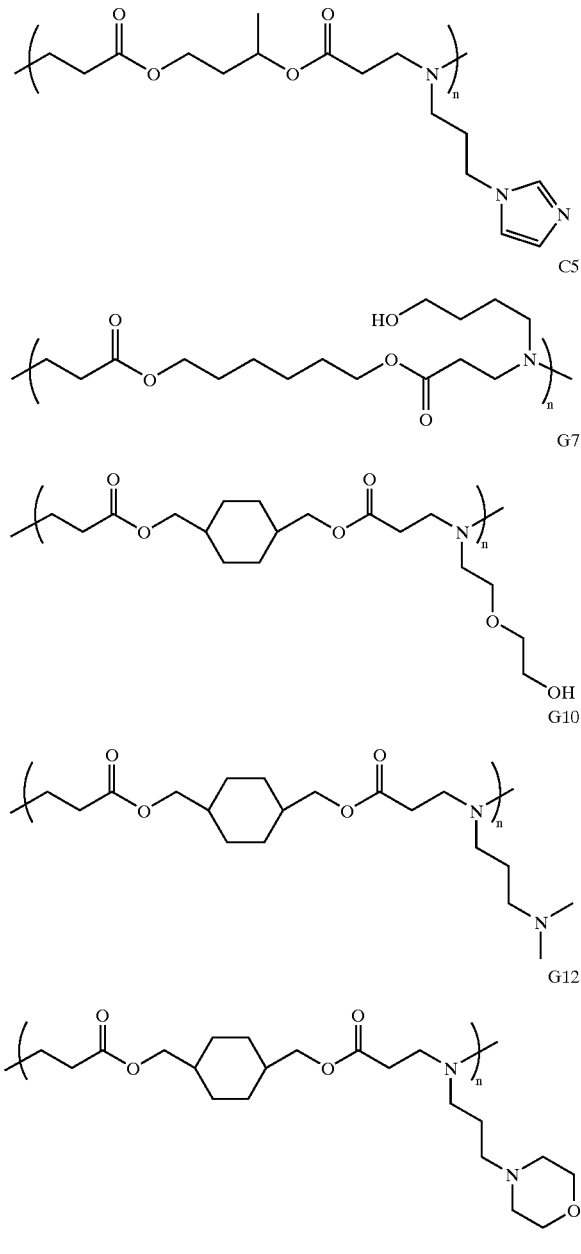

In a particularly preferred embodiment, one or both of the linkers A and B are polyethylene polymers. In another particularly preferred embodiment, one or both of the linkers A and B are polyethylene glycol polymers. Other biocompatible, biodegradable polymers may be used as one or both of the linkers A and B.

In another particularly preferred embodiment, the polymer of the present invention is a co-polymer wherein one of the repeating units is a poly(β-amino ester) of the present invention. Other repeating units to be used in the co-polymer include, but are not limited to, polyethylene, poly(glycolide-co-lactide) (PLGA), polyglycolic acid, polymethacrylate, etc.

Synthesis of Polymers

The inventive polymers may be prepared by any method known in the art. Preferably the polymers are prepared from commercially available starting materials. In another preferred embodiment, the polymers are prepared from easily and/or inexpensively prepared starting materials.

In a particularly preferred embodiment, the inventive polymer is prepared via the conjugate addition of bis(secondary amines) to bis(acrylate ester). This reaction scheme is shown below:

(Eq 1)

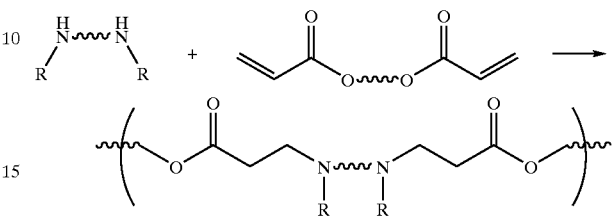

Bis(secondary amine) monomers that are useful in the present inventive method include, but are not limited to, N,N'-dimethylethylenediamine, piperazine, 2-methylpiperazine, 1,2-bis(N-ethylamino)ethylene, and 4,4'-trimethylenedipiperidine. Diacrylate monomers that are useful in the present invention include, but are not limited to, 1,4-butanediol diacrylate, 1,4-butanediol dimethacrylate, 1,2-ethanediol diacrylate, 1,6-hexanediol diacrylate, 2,5-hexanediol diacrylate, and 1,3-propanediol diacrylate. Each of the monomers is dissolved in an organic solvent (e.g., THF, $CH_2Cl_2$, MeOH, EtOH, $CHCl_3$, hexanes, toluene, benzene, $CCl_4$, glyme, diethyl ether, etc.). The resulting solutions are combined, and the reaction mixture is heated to yield the desired polymer. In a particularly preferred embodiment, the reaction mixture is heated to approximately 50° C. In another particularly preferred embodiment, the reaction mixture is heated to approximately 75° C. The polymerization reaction may also be catalyzed. As would be appreciated by one of skill in this art, the molecular weight of the synthesized polymer may be determined by the reaction conditions (e.g., temperature, starting materials, concentration, solvent, etc.) used in the synthesis.

In another particularly preferred embodiment, the inventive polymers are prepared by the conjugate addition of a primary amine to a bis(acrylate ester). The use of primary amines rather than bis(secondary amines) allows for a much wider variety of commercially available starting materials. The reaction scheme using primary amines rather than secondary amines is shown below:

(Eq .2)

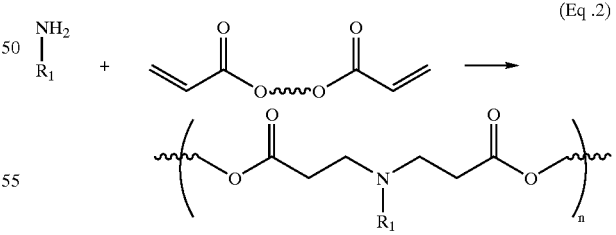

Primary amines useful in this method include, but are not limited to, methylamine, ethylamine, isopropylamine, aniline, substituted anilines, and ethanolamine. The bis(acrylate esters) useful in this method include, but are not limited to, 1,4-butanediol diacrylate, 1,4-butanediol dimethacrylate, 1,2-ethanediol diacrylate, 1,6-hexanediol diacrylate, 2,5-hexanediol diacrylate, and 1,3-propanediol diacrylate. Each of the monomers is dissolved in an organic solvent (e.g., THF, $CH_2Cl_2$, MeOH, EtOH, $CHCl_3$, hexanes, CCl$_4$, glyme, diethyl ether, etc.). Organic solvents are preferred due to the susceptibility of polyesters to hydrolysis. The resulting solutions are combined, and the reaction mixture is heated to yield the desired polymer. In a particularly preferred embodiment, the reaction mixture is maintained at 20° C. In another particularly preferred embodiment, the reaction mixture is heated to approximately 50° C. In yet another particularly preferred embodiment, the reaction mixture is heated to approximately 75° C. The reaction mixute may also be cooled to approximately 0° C. The polymerization reaction may also be catalyzed. In another preferred embodiment, one or more types of amine monomers and/or diacrylate monomers may be used in the polymerization reaction. For example, a combination of ethanolamine and ethylamine may be used to prepare a polymer more hydrophilic than one prepared using ethylamine alone, and also more hydrophobic than one prepared using ethanolamine alone.

The synthesized polymer may be purified by any technique known in the art including, but not limited to, precipitation, crystallization, chromatography, etc. In a particularly preferred embodiment, the polymer is purified through repeated precipitations in organic solvent (e.g., diethyl ether, hexane, etc.). In a particularly preferred embodiment, the polymer is isolated as a hydrochloride salt. As would be appreciated by one of skill in this art, the molecular weight of the synthesized polymer and the extent of cross-linking may be determined by the reaction conditions (e.g., temperature, starting materials, concentration, order of addition, solvent, etc.) used in the synthesis (Odian *Principles of Polymerization 3rd Ed.*, New York: John Wiley & Sons, 1991; Stevens *Polymer Chemistry: An Introduction 2nd Ed.*, New York: Oxford University Press, 1990; each of which is incorporated herein by reference).

In one embodiment a library of different polymers is prepared in parallel. A different amine and/or bis(acrylate ester) is added to each vial in a set of vials used to prepare the library. The array of vials is incubated at a temperature and length of time sufficient to allow polymerization of the monomers to occur. In one embodiment, the vials are incubated at approximately 45° C. for approximately 5 days. The polymers may then be isolated and purified using techniques known in the art. The polymers may then be screened using high-throughput techniques to identify polymers with a desired characteristic (e.g., solubility in water, solubility at different pH, ability to bind polynucleotides, ability to bind heparin, ability to bind small molecules, ability to form microparticles, ability to increase transfection efficiency, etc.). In certain embodiments the polymers may be screened for properties or characteristics useful in gene therapy (e.g., ability to bind polynucleotides, increase in transfection efficiency). In other embodiments the polymers may be screened for properties or characteristics useful in the art of tissue engineering (e.g., ability to support tissue or cell growth, ability to promote cell attachment).

Polynucleotide Complexes

The ability of cationic compounds to interact with negatively charged polynucleotides through electrostatic interactions is well known. Cationic polymers such as poly(lysine) have been prepared and studied for their ability to complex polynucleotides. However, polymers studied to date have incorporated amines at the terminal ends of short, conformationally flexible side chains (e.g., poly(lysine)) or accessible amines on the surface of spherical or globular polyamines (e.g., PEI and PAMAM dendrimers). The interaction of the polymer with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In a particularly preferred embodiment, the complex is slightly positively charged. In another particularly preferred embodiment, the complex has a postive ζ-potential, more preferably the ζ-potential is between +1 and +30.

The poly(β-amino esters) of the present invention possess tertiary amines in the backbone of the polymer. Although these amines are more hindered, they are available to interact with a polynucleotide. Polynucleotides or derivatives thereof are contacted with the inventive polymers under conditions suitable to form polynucleotide/polymer complexes. The polymer is preferably at least partially protonated so as to form a complex with the negatively charged polynucleotide. In a preferred embodiment, the polynucleotide/polymer complexes form nanoparticles that are useful in the delivery of polynucleotides to cells. In a particularly preferred embodiment, the diameter of the nanoparticles ranges from 50–500 nm, more preferably the diameter of the nanoparticles ranges from 50–200 nm, and most preferably from 90–150 nm. The nanoparticles may be associated with a targeting agent as described below.

Polynucleotide

The polynucleotide to be complexed or encapsulated by the inventive polymers may be any nucleic acid including but not limited to RNA and DNA. The polynucleotides may be of any size or sequence, and they may be single- or double-stranded. In certain preferred embodiments, the polynucleotide is greater than 100 base pairs long. In certain other preferred embodiments, the polynucleotide is greater than 1000 base pairs long and may be greater than 10,000 base pairs long. The polynucleotide is preferably purified and substantially pure. Preferably, the polynucleotide is greater than 50% pure, more preferably greater than 75% pure, and most preferably greater than 95% pure. The polynucleotide may be provided by any means known in the art. In certain preferred embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In a preferred embodiment, the polynucleotide is synthesized using standard solid phase chemistry.

The polynucleotide may be modified by chemical or biological means. In certain preferred embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolopyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain preferred embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In other particularly preferred embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al. *Nature* 391:806–811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1): 31–44, 1999; Crooke "Evaluating the mechanism of action of antiproliferative antisense drugs" *Antisense Nucleic Acid Drug Dev.* 10(2):123–126, discussion 127, 2000; *Methods in Enzymology* volumes 313–314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4): 267–282, 1997; incorporated herein by reference).

In a particularly preferred embodiment, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health and can be found on the World Wide Web (http:/www.niaid.nih.gov/daids/vaccine/pdf/compendium.pdf, incorporated herein by reference; see also Allison *Dev. Biol. Stand.* 92:3–11, 1998; Unkeless et al. *Annu. Rev. Immunol.* 6:251–281, 1998; and Phillips et al. *Vaccine* 10:151–158,1992, each of which is incorporated herein by reference).

The antigenic protein or peptides encoded by the polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni,* and the like; from such viruses as smallpox, influenza A and B, respiratory syncytial virus, parainfluenza, measles, HIV, *varicella-zoster*, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Microparticles

The poly($\beta$-amino esters) of the present invention may also be used to form drug delivery devices. The inventive polymers may be used to encapsulate agents including polynucleotides, small molecules, proteins, peptides, metals, organometallic compounds, etc. The inventive polymers have several properties that make them particularly suitable in the preparation of drug delivery devices. These include 1) the ability of the polymer to complex and "protect" labile agents; 2) the ability to buffer the pH in the endosome; 3) the ability to act as a "proton sponge" and cause endosomolysis; and 4) the ability to neutralize the charge on negatively charged agents. In a preferred embodiment, the polymers are used to form microparticles containing the agent to be delivered. In a particularly preferred embodiment, the diameter of the microparticles ranges from between 500 nm to 50 micrometers, more preferably from 1 micrometer to 20 micrometers, and most preferably from 1 micrometer to 10 micrometers. In another particularly preferred embodiment, the microparticles range from 1–5 micrometers. The encapsulating inventive polymer may be combined with other polymers (e.g., PEG, PLGA) to form the microspheres.

Methods of Preparing Microparticles

The inventive microparticles may be prepared using any method known in this art. These include, but are not limited to, spray drying, single and double emulsion solvent evaporation, solvent extraction, phase separation, simple and complex coacervation, and other methods well known to those of ordinary skill in the art. Particularly preferred methods of preparing the particles are the double emulsion process and spray drying. The conditions used in preparing the microparticles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the polymer matrix.

Methods developed for making microparticles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13–22, 1987; Mathiowitz et al. *Reactive Polymers* 6:275–283, 1987; Mathiowitz et al. *J. Appl. Polymer Sci.* 35:755–774, 1988; each of which is incorporated herein by reference).

If the particles prepared by any of the above methods have a size range outside of the desired range, the particles can be sized, for example, using a sieve.

Agent

The agents to be delivered by the system of the present invention may be therapeutic, diagnostic, or prophylactic agents. Any chemical compound to be administered to an individual may be delivered using the inventive microparticles. The agent may be a small molecule, organometallic compound, nucleic acid, protein, peptide, polynucleotide, metal, an isotopically labeled chemical compound, drug, vaccine, immunological agent, etc.

In a preferred embodiment, the agents are organic compounds with pharmaceutical activity. In another embodiment of the invention, the agent is a clinically used drug. In a particularly preferred embodiment, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In a preferred embodiment of the present invention, the agent to be delivered may be a mixture of agents. For example, a local anesthetic may be delivered in combination with an anti-inflammatory agent such as a steroid. Local anesthetics may also be administered with vasoactive agents such as epinephrine. To give another example, an antibiotic may be combined with an inhibitor of the enzyme commonly produced by bacteria to inactivate the antibiotic (e.g., penicillin and clavulanic acid).

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponemapallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, *varicella-zoster*, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents

The inventive micro- and nanoparticles may be modified to include targeting agents since it is often desirable to target a particular cell, collection of cells, or tissue. A variety of targeting agents that direct pharmaceutical compositions to particular cells are known in the art (see, for example, Cotten et al. *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferring, asialycoproteins, gp120 envelope protein of the human immunodeficiency virus (HIV), carbohydrates, receptor ligands, sialic acid, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen boding, van der Waals, or other interactions) the formed particles using standard chemical techniques.

Pharmaceutical Compositions

Once the microparticles or nanoparticles (polymer complexed with polynucleotide) have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, polynucleotide/polymer complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the microparticles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

These and other aspects of the present invention will be further appreciated upon consideration of the following Examples, which are intended to illustrate certain particular embodiments of the invention but are not intended to limit its scope, as defined by the claims.

EXAMPLES

Example 1

Degradable Poly(β-Amino Esters): Synthesis, Characterization, and Self-Assembly with Plasmid DNA Experimental Section General Considerations. All manipulations involving live cells or sterile materials were performed in a laminar flow using standard sterile technique. $^1$H NMR (300.100 MHz) and $^{13}$C NMR (75.467 MHz) spectra were recorded on a Varian Mercury spectrometer. All chemical shift values are given in ppm and are referenced with respect to residual proton or carbon signal from solvent. Organic phase gel permeation chromatography (GPC) was performed using a Hewlett Packard 1100 Series isocratic pump, a Rheodyne Model 7125 injector with a 100-μL injection loop, and two PL-Gel mixed-D columns in series (5 μm, 300×7.5 mm, Polymer Laboratories, Amherst, Mass.). THF/0.1 M piperidine was used as the eluent at a flow rate of 1.0 mL/min. Data was collected using an Optilab DSP interferometric refractometer (Wyatt Technology, Santa Barbara, Calif.) and processed using the TriSEC GPC software package (Viscotek Corporation, Houston, Tex.). The molecular weights and polydispersities of the polymers are reported relative to monodispersed polystyrene standards. Aqueous phase GPC was performed by American Polymer Standards (Mentor, Ohio) using Ultrahydrogel L and 120A columns in series (Waters Corporation, Milford, Mass.). Water (1% acetic acid, 0.3 M NaCl) was used as the eluent at a flow rate of 1.0 mL/min. Data was collected using a Knauer differential refractometer and processed using an IBM/PC GPC-PRO 3.13 software package (Viscotek Corporation, Houston, Tex.). The molecular weights and polydispersities of the polymers are reported relative to poly(2-vinylpyridine) standards. For cytotoxicity assays, absorbance was measured using a Dynatech Laboratories MR5000 microplate reader at 560 mn.

Materials. N,N'-dimethylethylenediamine, piperazine, and 4,4'-trimethylenedipiperidine were purchased from Aldrich Chemical Company (Milwaukee, Wis.). 1,4-butanediol diacrylate was purchased from Alfa Aesar Organics (Ward Hill, Mass.). (3-[4,5-dimethylthiazol-2-yl]-2,5-diphenyltetrazolium bromide (MTT) was purchased from Sigma Chemical Company (St. Louis, Mo.). Plasmid DNA (pCMV-Luc) was produced in E. coli (DH5α, a kind gift from Zycos, Inc., Cambridge, Mass.), isolated with a Qiagen kit, and purified by ethanol precipitation. NIH 3T3 cells were purchased from American Type Culture Collection (Manassas, Va.) and grown at 37° C., 5% $CO_2$ in Dulbecco's modified Eagle's medium, 90%; fetal bovine serum, 10%; penicillin, 100 units/mL; streptomycin, 100 μg/mL. All other materials and solvents were used as received without further purification.

General Polymerization Procedure. In a typical experiment, 1,4-butanediol diacrylate (0.750 g, 0.714 mL, 3.78 mmol) and diamine (3.78 mmol) were weighed into two separate vials and dissolved in THF (5 mL). The solution containing the diamine was added to the diacrylate solution via pipette. A Teflon-coated stirbar was added, the vial was sealed with a Teflon-lined screw-cap, and the reaction was heated at 50° C. After 48 hours, the reaction was cooled to room temperature and dripped slowly into vigorously stirring diethyl ether or hexanes. Polymer was collected and dried under vacuum prior to analysis.

Synthesis of Polymer 1. Polymer 1 was prepared according to the general procedure outlined above. $^1$H NMR δ ($CDCl_3$, 300 MHz) 4.11 (br t, 4H), 2.75 (br t, J=7.05 Hz, 4 H), 2.53 (br s, 4H), 2.50 (br t, (obsc), J=7.20 Hz, 4H), 2.28 (br s, 6H), 1.71, (br m, 4H). $^{13}$C NMR δ ($CDCl_3$, 75.47 MHz) 172.55, 64.14, 55.31, 53.39, 42.47, 32.54, 25.53.

Synthesis of Polymer 2. Polymer 2 was prepared according to the general procedure outlined above. $^1$H NMR δ ($CDCl_3$, 300 MHz) 4.11 (br t, 4H), 2.74 (br t, J=7.35, 4H), 2.56 (br m, 12H), 1.71 (br t, 4H). $^{13}$C NMR δ ($CDCl_3$, 75.47 MHz) 172.24, 64.19, 53.55, 52.75, 32.27, 25.52.

Synthesis of Polymer 3. Polymer 3 was prepared according to the general procedure outlined above. $^1$H NMR δ ($CDCl_3$, 300 MHz) 4.11 (br t, 4H), 3.00 (br m, 4H), 2.79 (br m, 4H), 2.65 (br m, 4H), 2.11 (br m, 4H), 1.70 (br m, 8H), 1.25 (br m, 12H). $^{13}$C NMR δ ($CDCl_3$, 75.47 MHz) 172.37, 64.13, 53.89 (br), 36.74, 35.58, 32.11 (br), 25.45, 24.05.

Polymer Degradation Studies. The hydrochloride salts of polymers 1–3 were dissolved in acetate buffer (1 M, pH=5.1) or HEPES buffer (1 M, pH=7.4) at a concentration of 5 mg/mL (the use of millimolar concentrations of buffer resulted in substantial reduction of pH during degradation due to the production of acidic degradation products). Samples were incubated at 37° C. on a mechanical rotator, and aliquots (1 mL) were removed at appropriate time intervals. Aliquots were frozen immediately in liquid nitrogen and lyophilized. Polymer was extracted from dried buffer salts using THF/0.1 M piperidine (1 mL), and samples were analyzed directly by GPC.

Formation of DNA/Polymer Complexes and Agarose Gel Retardation Assays.

DNA/polymer complexes were formed by adding 50 μL of a plasmid DNA solution (pCMV Luc, 2 μg/50 μL in water) to a gently vortexing solution of the hydrochloride salt of polymers 1–3 (50 μL in 25 mM MES, pH=6.0, concentrations adjusted to yield desired DNA/polymer weight ratios). The samples were incubated at room temperature for 30 minutes, after which 20 μL was run on a 1% agarose gel (HEPES, 20 mM, pH=7.2, 65V, 30 min). Samples were loaded on the gel with a loading buffer consisting of 10% Ficoll 400 (Amersham Pharmacia Biotech, Uppsala, Sweden) in HEPES (25 mM, pH=7.2). Bromphenol blue was not included as a visual indicator in the loading buffer, since this charged dye appeared to interfere with the complexation of polymer and DNA. DNA bands were visualized under UV illumination by ethidium bromide staining.

Quasi-Elastic Laser Light Scattering (QELS) and Measurement of ζ-potentials. QELS experiments and ζ-potential measurements were made using a ZetaPALS dynamic light scattering detector (Brookhaven Instruments Corporation, Holtsville, N.Y., 15 mW laser, incident beam=676 nm). DNA/polymer complexes were formed as described above for agarose gel retardation assays. Samples were diluted with 900 μL of HEPES (20 mM, pH=7.0), added to a gently vortexing sample of DNA/polymer complex (total volume=1 mL, pH=7.0). Average particle sizes and ζ-potentials were determined at 25° C. Correlation functions were collected at a scattering angle of 90°, and particle sizes were calculated using the MAS option of BIC's particle sizing software (ver. 2.30) using the viscosity and refractive index of pure water at 25° C. Particle sizes are expressed as effective diameters assuming a lognormal distribution. Average electrophoretic mobilities were measured at 25° C. using BIC PALS zeta potential analysis software and zeta potentials were calculated using the Smoluchowsky model for aqueous suspensions. Three measurements were made on each sample, and the results are reported as average diameters and zeta potentials.

Cytotoxicity Assays. Immortalized NIH 3T3 cells were grown in 96-well plates at an initial seeding density of 10,000 cells/well in 200 $\mu$L growth medium (90% Dulbecco's modified Eagle's medium, 10% fetal bovine serum, penicillin 100 units/mL, streptomycin 100 $\mu$g/mL). Cells were grown for 24 hours, after which the growth medium was removed and replaced with 180 $\mu$L of serum-free medium. Appropriate amounts of polymer were added in 20 $\mu$L aliquots. Samples were incubated at 37° C. for 5 hours, and the metabolic activity of each well was determined using a MTT/thiazolyl blue assay: to each well was added 25 $\mu$L of a 5 mg/mL solution of MTT stock solution in sterile PBS buffer. The samples were incubated at 37° C. for 2 hours, and 100 $\mu$L of extraction buffer (20% w/v SDS in DMF/water (1:1), pH=4.7) was added to each well. Samples were incubated at 37° C. for 24 hours. Optical absorbance was measured at 560 nm with a microplate reader and expressed as a percent relative to control cells.

Results and Discussion

Polymer Synthesis and Characterization

The synthesis of linear poly(amido amines) containing tertiary amines in their backbones was reported by Ferruti et al. in 1970 via the addition of bifunctional amines to bisacrylamides (Anderson *Nature* 392(Suppl.):25–30, 1996; Friedman *Nature Med.* 2:144–147, 1996; Crystal *Science* 270:404–410, 1995; Mulligan *Science* 260:926–932, 1993; each of which is incorporated herein by reference). Linear poly(amido amines) were initially investigated as heparin and ion complexing biomaterials (Ferruti et al. *Advances in Polymer Science* 58:55–92, 1984; Ferruti et al. *Biomaterials* 15:1235–1241, 1994; Ferruti et al. *Macromol. Chem. Phys.* 200:1644–1654, 1999; Ferruti et al. *Biomaterials* 15:1235–1241, 1994; each of which is incorporated herein by reference). Dendritic poly(amido amines) (PAMAMs) have seen increasing use in gene transfer applications due to their ability to complex DNA (Kukowska-Latallo et al. *Proc. Natl. Acad. Sci. USA* 93:4897–4902, 1996; Tang et al. *Bioconjugate Chem.* 7:703–714, 1996; Haensler et al. *Bioconjugate Chem.* 4:372–379, 1993; each of which is incorporated herein by reference), and a recent report describes the application of a family of linear poly(amido amines) to cell transfection and cytotoxicity studies (Hill et al. *Biochim. Biophys. Acta* 1427:161–174, 1999; incorporated herein by reference). In contrast, analogous poly(ester amines) formed from the Michael-type addition of bifunctional amines to diacrylate esters have received less attention (Danusso et al. *Polymer* 11:88–113, 1970; Ferruti et al. *Polymer* 26:1336, 1985; Ferruti et al. *Advances in Polymer Science* 58:55–92, 1984; Ferruti et al. *Biomaterials* 15:1235–1241, 1994; Ferruti et al. *Macromol. Chem. Phys.* 200:1644–1654, 1999; Ferruti et al. *Biomaterials* 15:1235–1241, 1994; Kargina et al. *Vysokomol. Soedin. Seriya A* 28:1139–1144, 1986; Rao et al. *J. Bioactive and Compatible Polymers* 14:54–63, 1999; each of which is incorporated herein by reference).

The poly(amino ester) approach presents a particularly attractive basis for the development of new polymeric transfection vectors for several reasons: 1) the polymers contain the requisite amines and readily degradable linkages, 2) multiple analogs could potentially be synthesized directly from commercially available starting materials, and 3) if the resulting polymers were useful as DNA condensing agents, future generations of polymer could easily be engineered to possess amine $pK_a$ values spanning the range of physiologically relevant pH. This last point was particularly intriguing, because the buffering capacity of polyamines has recently been implicated as a factor influencing the escape of DNA from cell endosomes following endocytosis (Boussif et al. *Proc. Natl. Acad. Sci. USA* 92:7297–7301, 1995; Haensler et al. *Bioconjugate Chem.* 4:372–379, 1993; Behr *Chimia* 51:34–36, 1997; Demeneix et al., in *Artificial Self-Assembling Systems for Gene Delivery* (Felgner et al., Eds.), American Chemical Society, Washington, D.C., 1996, pp. 146–151; Kabanov et al., in *Self-Assembling Complexes for Gene Delivery: From Laboratory to Clinical Trial*, John Wiley and Sons, New York, 1998; each of which is incorporated herein by reference). While the complexation of DNA with a cationic polymer is required to compact and protect DNA during early events in the transfection process, DNA and polymer must ultimately decomplex in the nucleus to allow efficient transcription (Luo et al. *Nat. Biotechnol.* 18:33–37, 2000; incorporated herein by reference). In view of this requirement, degradable polycations could play an important role in "vector unpackaging" events in the nucleus (Luo et al. *Nat. Biotechnol.* 18:33–37, 2000; Schaffer et al. *Biotechnol. Bioeng.* 67:598–606, 2000; Kabanov *Pharm. Sci. Technol. Today* 2:365–372, 1999; each of which is incorporated herein by reference). Finally, we hypothesized that polymers of this general structure, and the β-amino acid derivatives into which they would presumably degrade, would be significantly less toxic than poly(lysine) and PEI. As outlined above, degradable polycations (Putnam et al *Macromolecules* 32:3658–3662, 1999; Lim et al. *J. Am. Chem. Soc.* 121:5633–5639, 1999; Lim et al. *J. Am. Chem. Soc.* 122:6524–6525, 2000; each of which is incorporated herein by reference) and linear polymers containing relatively hindered amines located close to the polymer backbone (Gonzalez et al. *Bioconjugate Chem.* 10:1068–1074, 1999; incorporated herein by reference) are less toxic than poly(lysine) and PEI.

The synthesis of polymers 1–3 via the addition of the bis(secondary amines), N,N'-dimethylethylenediamine, piperazine, and 4,4'-trimethylenedipiperidine, to 1,4-butanediol diacrylate was investigated (Danusso et al. *Polymer* 11:88–113, 1970; Kargina et al. *Vysokomol. Soedin. Seriya A* 28:1139–1144, 1986; each of which is incorporated herein by reference). The polymerization of these monomers proceeded in THF and $CH_2Cl_2$ at 50° C. to yield the corresponding polymers in up to 86% yields (Table 1). Polymers were purified through repeated precipitation into diethyl ether or hexane. Polymer 1 was isolated as a clear viscous liquid; polymers 2 and 3 were obtained as white solids after drying under high vacuum. Alternatively, polymers 1–3 could be isolated as solid hydrochloride salts upon addition of diethyl ether/HCl to a solution of polymer in THF or $CH_2Cl_2$. All three polymers were soluble in organic solvents such as THF, $CH_2Cl_2$, $CHCl_3$, and MeOH and were also soluble in water at reduced pH. Polymer 1 and the hydrochloride salts of polymers 1–3 were freely soluble in water.

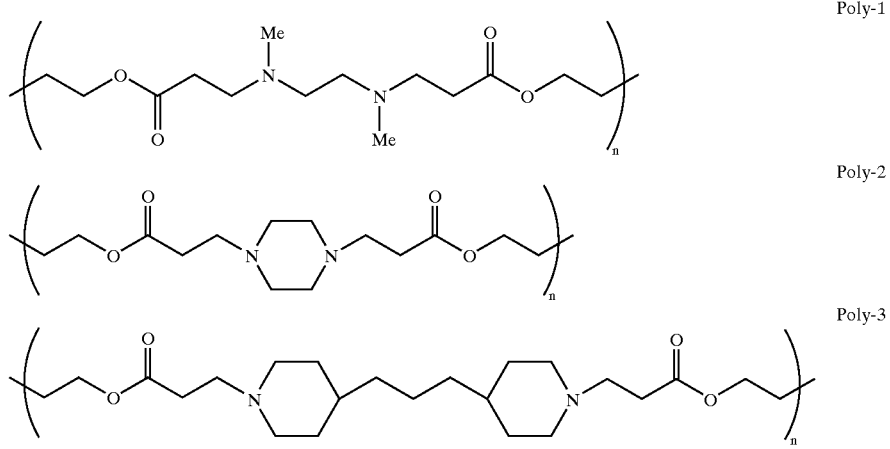

The molecular weights of polymers 1–3 and their corresponding hydrochloride salts were determined by both organic and aqueous phase gel permeation chromatography (GPC). Polymer molecular weights ($M_n$) ranged from up to 5,800 for polymer 1 to up to 32,000 for polymer 3, relative to polystyrene standards. Molecular weight distributions for these polymers were monomodal with polydispersity indices (PDIs) ranging from 1.55 to 2.55. Representative molecular weight data are presented in Table 1. While the synthesis of linear poly(amido amines) is generally performed using alcohols or water as solvents (Danusso et al. *Polymer* 11:88–113, 1970; Ferruti et al. *Polymer* 26:1336, 1985; Ferruti et al. *Advances in Polymer Science* 58:55–92, 1984; Ferruti et al. *Biomaterials* 15:1235–1241, 1994; Ferruti et al. *Macromol. Chem. Phys.* 200:1644–1654, 1999; Ferruti et al. *Biomaterials* 15:1235–1241, 1994; each of which is incorporated herein by reference), anhydrous THF and $CH_2Cl_2$ were employed in the synthesis of poly(β-amino esters) to minimize hydrolysis reactions during the synthesis. The yields and molecular weights of polymers synthesized employing $CH_2Cl_2$ as solvent were generally higher than those of polymers synthesized in THF (Table 1) (Polymer 1 could not by synthesized in $CH_2Cl_2$. The color of the reaction solution progressed from colorless to an intense pink color almost immediately after the introduction of a solution of N,N'-dimethylethylenediamine in $CH_2Cl_2$ to a solution of 1,4-butanediol diacrylate in $CH_2Cl_2$ (see Experimental Section above). The color progressed to light orange over the course of the reaction, and an orange polymer was isolated after precipitation into hexane. The isolated polymer was insoluble in $CH_2Cl_2$, THF, and water at reduced pH and was not structurally characterized. This problem was not encountered for the analogous reaction in THF.).

TABLE 1

Representative Molecular Weight Data for Polymers 1–3.

| Polymer | Solvent | $M_n{}^c$ | PDI | Yield, % |
|---|---|---|---|---|
| 1[a] | THF | — | — | —[d] |
| 1[a] | $CH_2Cl_2$ | — | — | 82% |
| 2[a] | THF | 10000 | 1.77 | 64% |
| 2[a] | $CH_2Cl_2$ | 17500 | 2.15 | 75% |
| 3[a] | THF | 24400 | 1.55 | 58% |
| 3[a] | $CH_2Cl_2$ | 30800 | 2.02 | 70% |
| 1[b] | THF | 5800 | 2.83 | 55% |

TABLE 1-continued

Representative Molecular Weight Data for Polymers 1–3.

| Polymer | Solvent | $M_n{}^c$ | PDI | Yield, % |
|---|---|---|---|---|
| 2[b] | $CH_2Cl_2$ | 16500 | 2.37 | 80%[e] |
| 3[b] | $CH_2Cl_2$ | 31200 | 2.55 | 86%[e] |

[a]Conditions: [diamine] = [1,4-butanediol diacrylate] = 0.38 M, 50° C., 48 h.
[b]Conditions: [diamine] = [1,4-butanediol diacrylate] = 1.08 M, 50° C., 48 h.
[c]GPC analysis was performed in THF/0.1 M piperidine and molecular weights are reported versus polystyrene standards.
[d]No polymer was isolated under these conditions.
[e]The reaction solution became very viscous and eventually solidified under these conditions.

The structures of polymers 1–3 were confirmed by $^1$H and $^{13}$C NMR spectroscopy. These data indicate that the polymers were formed through the conjugate addition of the secondary amines to the acrylate moieties of 1,4-butanediol diacrylate and not through the formation of amide linkages under our reaction conditions. Additionally, the newly formed tertiary amines in the polymer backbones do not participate in subsequent addition reactions with diacrylate monomer, which would lead to branching or polymer crosslinking. This fortunate result appears to be unique to polymers of this type produced from bis(secondary amine) monomers. The synthesis of analogous polymers employing difunctional primary amines as monomers (such as 1,4-diaminobutane) may lead to polymer branching and the formation of insoluble crosslinked polymer networks if conditions are not explicitly controlled.

In view of the juxtaposition of amines and esters within the backbones of polymers 1–3, we were initially concerned that hydrolysis might occur too rapidly for the polymers to be of practical use. For example, poly(4-hydroxy-L-proline ester) and poly[α-(4-aminobutyl)-L-glycolic acid] degrade quite rapidly near neutral pH, having half lives of roughly 2 hr (Lim et al. *J. Am. Chem. Soc.* 121:5633–5639, 1999; incorporated herein by reference) and 30 min (Lim et al. *J. Am. Chem. Soc.* 122:6524–6525, 2000; incorporated herein by reference), respectively (Such rapid degradation times did not preclude the application of these polymers to gene delivery (See references, Lim et al. *J. Am. Chem. Soc.* 121:5633–5639, 1999; Lim et al. *J. Am. Chem. Soc.* 122:6524–6525, 2000; each of which is incorporated herein by reference). However, extremely rapid degradation rates generally introduce additional concerns surrounding the manipulation, storage, and application of degradable polymers.). Analysis of polymers 1 and 2 by aqueous GPC using 1% acetic acid/water as eluent, however, revealed that degradation was sufficiently slow in acidic media. For example, the GPC traces of polymers 1 and 2 sampled under these conditions over a period of 4–5 hours revealed no changes in molecular weights or polydispersities (Polymer 3 could not be analyzed by aqueous GPC.). We were also concerned that significant backbone hydrolysis might occur during the isolation of the hydrochloride salts of polymers 1–3. To prevent hydrolysis during the protonation and isolation of these polymers, anhydrous solvents were employed and reactions were performed under an argon atmosphere. Analysis of the polymers before and after protonation revealed no observable hydrolysis. For example, the GPC trace of a sample of polymer 3 after precipitation from $CH_2Cl_2$ with 1.0 M diethyl ether/HCl ($M_n$=15,300; PDI=1.90) was virtually identical to the molecular weight of the polymer prior to protonation ($M_n$=15,700; PDI=1.92) and no lower molecular weight species were evident (Comparative GPC data were collected employing THF/0.1M piperidine as eluent (see Experimental Section above). The HCl salts of the polymers were insoluble in THF, but were soluble in THF/0.1 M piperidine concomitant with the production of a fine white precipitate which was filtered prior to injection.). Solid samples of polymers 1–3 could be stored for several months without detectable decreases in molecular weight.

Polymers 1–3 were specifically designed to degrade via hydrolysis of the ester bonds in the polymer backbones. However, an additional concern surrounding the overall stability and biocompatibility of these polymers is the potential for unwanted degradation to occur through retro-Michael reaction under physiological conditions. Because these polymers were synthesized via the Michael-type reaction of a secondary amine to an acrylate ester, it is possible that the polymers could undergo retro-Michael reaction to regenerate free acrylate groups, particularly under acidic conditions. Acrylate esters are potential DNA-alkylating agents and are therefore suspected carcinogens (for recent examples, see: Schweikl et al. *Mutat. Res.* 438:P71–P78, 1999; Yang et al. *Carcinogenesis* 19:P1117–P1125, 1998; each of which is incorporated herein by reference). Because these polymers are expected to encounter the reduced pH environment within the endosomal vesicles of cells (pH= 5.0–5.5) during transfection, we addressed the potential for the degradation of these polymers to occur through a retro-Michael pathway.

Under extremely acidic (pH<3) or basic (pH>12) conditions, polymers 1–3 degraded rapidly and exclusively to 1,4-butanediol and the anticipated bis(β-amino acid) byproducts 4a–6a as determined by $^1H$ NMR spectroscopy. No spectroscopic evidence for retro-Michael addition under these conditions was found. It is worth noting that bis(β-amino acid) degradation products 4a–6a would be less likely to undergo a retro-Michael reaction, as acrylic acids are generally less activated Michael addition partners (Perlmutter, P., in *Conjugate Addition Reactions in Organic Synthesis*, Pergamon Press, New York, 1992; incorporated herein by reference). Further degradation of compounds 4a–6a under these conditions was not observed.

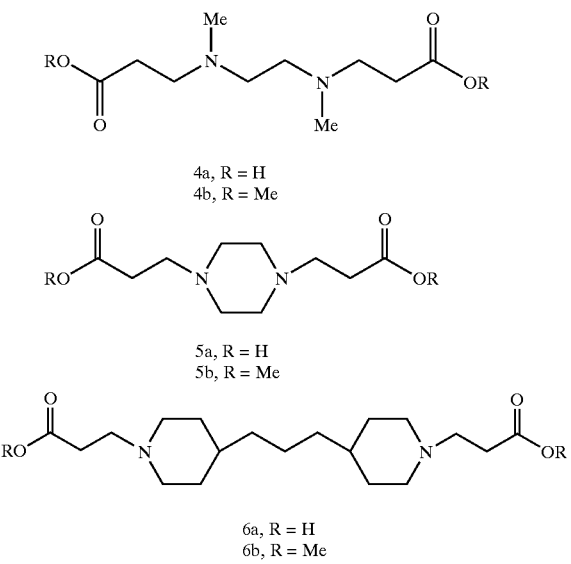

4a, R = H
4b, R = Me

5a, R = H
5b, R = Me

6a, R = H
6b, R = Me

The kinetics of polymer degradation were investigated under the range of conditions likely to be encountered by these polymers during transfection. Degradation was monitored at 37° C. at buffered pH values of 5.1 and 7.4 in order to approximate the pH of the environments within endosomal vesicles and the cytoplasm, respectively. The hydrochloride salts of polymers 1–3 were added to the appropriate buffer, incubated at 37° C., and aliquots were removed at appropriate times. Aliquots were frozen immediately, lyophilized, and polymer was extracted into THF/0.1 M piperidine for analysis by GPC. FIG. 1 shows the degradation profiles of polymers 1–3 as a function of time. The polymers degraded more slowly at pH 5.1 than at pH 7.4. Polymers 1–3 displayed similar degradation profiles at pH 5.1, each polymer having a half-life of approximately 7–8 hours. In contrast, polymers 1 and 3 were completely degraded in less than 5 hours at pH 7.4. These results are consistent with the pH-degradation profiles of other amine-containing polyesters, such as poly(4-hydroxy-L-proline ester), in which pendant amine functionalities are hypothesized to act as intramolecular nucleophilic catalysts and contribute to more rapid degradation at higher pH (Lim et al. *J. Am. Chem. Soc.* 121:5633–5639, 1999; Lim et al. *J. Am. Chem. Soc.* 122:6524–6525, 2000; each of which is incorporated herein by reference). While the possibility of intramolecular assistance cannot be ruled out, it is less likely for polymers 1–3 because the tertiary amines in these polymers should be less nucleophilic. The degradation of polymer 2 occurred more slowly at pH 7.4 than at pH 5.1 (FIG. 1). This anomalous behavior is most likely due to the incomplete solubility of polymer 2 at pH 7.4 and the resulting heterogeneous nature of the degradation milieu (Polymers 2 and 3 are not completely soluble in water at pH 7.4. While polymer 3 dissolved relatively rapidly during the degradation experiment, solid particles of polymer 2 were visible for several days.

Cytotoxicity Assays

Poly(lysine) and PEI have been widely studied as DNA condensing agents and transfection vectors (Luo et al. *Nat. Biotechnol.* 18:33–37, 2000; Behr *Acc. Chem. Res.* 26:274–278, 1993; Zauner et al. *Adv. Drug Del. Rev.* 30:97–113, 1998; Kabanov et al. *Bioconjugate Chem.* 6:7–20, 1995; Boussif et al. *Proc. Natl. Acad. Sci. USA* 92:7297–7301, 1995; Behr *Chimia* 51:34–36, 1997; Demeneix et al., in *Artificial Self-Assembling Systems for Gene Delivery* (Felgner et al., Eds.), American Chemical Society, Washington, D.C., 1996, pp. 146–151; Kabanov et al., in *Self-Assembling Complexes for Gene Delivery: From Laboratory to Clinical Trial*, John Wiley and Sons, New York, 1998; each of which is incorporated herein by reference) and are the standards to which new polymeric vectors are often compared (Putnam et al. *Macromolecules* 32:3658–3662, 1999; Lim et al. *J. Am. Chem. Soc.* 121:5633–5639, 1999; Lim et al. *J. Am. Chem. Soc.* 122:6524–6525, 2000; Gonzalez et al. *Bioconjugate Chem.* 10: 1068–1074, 1999; each of which is incorporated herein by reference). Unfortunately, as outlined above, these polymers are also associated with significant levels of cytotoxicity and high levels of gene expression are usually realized only at a substantial cost to cell viability. To determine the toxicity profile of polymers 1–3, a MTT/thiazolyl blue dye reduction assay using the NIH 3T3 cell line and the hydrochloride salts of polymers 1–3 was conducted as an initial indicators. The 3T3 cell line is commonly employed as a first level screening population for new transfection vectors, and the MTT assay is generally used as an initial indicator of cytotoxicity, as it determines the influences of added substances on cell growth and metabolism (Hansen et al. *Immunol. Methods* 119:203–210, 1989; incorporated herein by reference).

Figure 2:
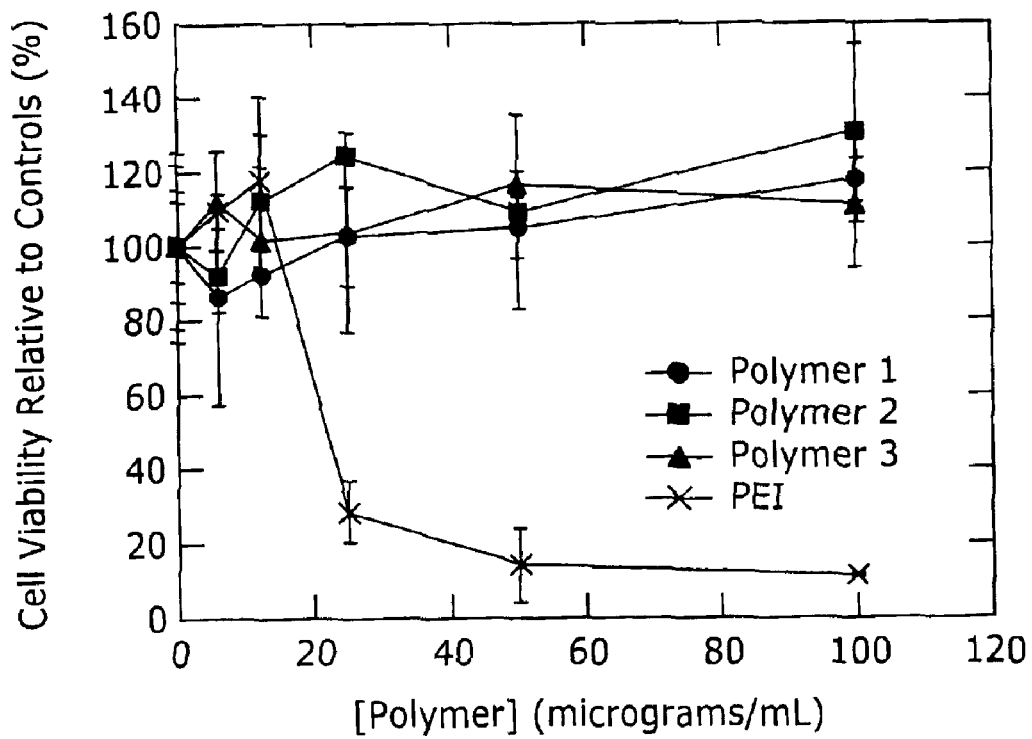
FIG. 2 shows cytotoxicity profiles of polymers 1–3 and PEI. Viability of NIH 3T3 cells is expressed as a function of polymer concentration. The molecular weights of polymers 1, 2, and 3 were 5800, 11300, and 22500, respectively. The molecular weight of the PEI employed was 25000.

Cells were incubated with polymer 1 ($M_n$=5 800), polymer 2 ($M_n$=11 300), and polymer 3 ($M_n$=22 500) as described in the Experimental Section. As shown in FIG. 2, cells incubated with these polymers remained 100% viable relative to controls at concentrations of polymer up to 100 µg/mL. These results compare impressively to data obtained for cell populations treated with PEI ($M_n$≈25 000), included as a positive control for our assay as well as to facilitate comparison to this well-known transfection agent. Fewer than 30% of cells treated with PEI remained viable at a polymer concentration of 25 µg/mL, and cell viability was as low as 10% at higher concentrations of PEI under otherwise identical conditions. An analogous MTT assay was performed using independently synthesized bis(β-amino acid)s 4a–6a to screen the cytotoxicity of the hydrolytic degradation products of these polymers. (Bis(β-amino acid)s 4a–6a should either be biologically inert or possess mild or acute toxicities which are lower than traditional polycationic transfection vectors. In either case, the degradation of these materials should facilitate rapid metabolic clearance.). Compounds 4a–6a and 1,4-butanediol did not perturb cell growth or metabolism in this initial screening assay (data not shown). A more direct structure/function-based comparison between polymers 1–3 and PEI cannot be made due to differences in polymer structure and molecular weight, both of which contribute to polycation toxicity. Nonetheless, the excellent cytotoxicity profiles of polymers 1–3 alone suggested that they were interesting candidates for further study as DNA condensing agents.

Self Assembly of Polymers 1–3 with Plasmid DNA

The tendency of cationic polyamines to interact electrostatically with the polyanionic backbone of DNA in aqueous solution is well known. Provided that the polymers are sufficiently protonated at physiological pH, and that the amines are sterically accessible, such interactions can result in a self-assembly process in which the positively and negatively charged polymers form well-defined conjugates (Kabanov et al., in *Self-Assembling Complexes for Gene Delivery: From Laboratory to Clinical Trial*, John Wiley and Sons, New York, 1998; each of which is incorporated herein by reference). The majority of polyamines investigated as DNA-complexing agents and transfection vectors have incorporated amines at the terminal ends of short, conformationally flexible side chains (e.g., poly(lysine) and methacrylate/methacrylamide polymers) (Zauner et al. *Adv. Drug Del. Rev.* 30:97–113, 1998; Kabanov et al. *Bioconjugate Chem.* 6:7–20, 1995; van de Wetering et al. *Bioconjugate Chem.* 10:589–597, 1999; each of which is incorporated herein by reference), or accessible amines on the surfaces of spherical or globular polyamines (e.g., PEI and PAMAM dendrimers) (Boussif et al. *Proc. Natl. Acad. Sci. USA* 92:7297–7301, 1995; Kukowska-Latallo et al. *Proc. Natl. Acad. Sci. USA* 93:4897–4902, 1996; Tang et al. *Bioconjugate Chem.* 7:703–714, 1996; Haensler et al. *Bioconjugate Chem.* 4:372–379, 1993; each of which is incorporated herein by reference). Because polymers 1–3 contain tertiary amines, and those tertiary amines are located in a sterically crowded environment (flanked on two sides by the polymer backbones), we were initially concerned that the protonated amines might not be sufficiently able to interact intimately with DNA.

The ability of polymers 1–3 to complex plasmid DNA was demonstrated through an agarose gel shift assay. Agarose gel electrophoresis separates macromolecules on the basis of both charge and size. Therefore, the immobilization of DNA on an agarose gel in the presence of increasing concentrations of a polycation has been widely used as an assay to determine the point at which complete DNA charge neutralization is achieved (Putnam et al. *Macromolecules* 32:3658–3662, 1999; Lim et al. *J. Am. Chem. Soc.* 121:5633–5639, 1999; Lim et al. *J. Am. Chem. Soc.* 122:6524–6525, 2000; Gonzalez et al. *Bioconjugate Chem.* 10:1068–1074, 1999; each of which is incorporated herein by reference). As mentioned above, the hydrochloride salts of polymers 1–3 are soluble in water. However, polymers 2 and 3 are not completely soluble at pH 7.2 over the full range of desired polymer concentrations. Therefore, DNA/polymer complexes were prepared in MES buffer (25 mM, pH=6.0). DNA/polymer complexes were prepared by adding an aqueous solution of DNA to vortexing solutions of polymer in MES at desired DNA/polymer concentrations (see Experimental Section). The resulting DNA/polymer complexes remained soluble upon dilution in the electrophoresis running buffer (20 mM HEPES, pH=7.2) and data were obtained at physiological pH. As a representative example, FIG. 3 depicts the migration of plasmid DNA (pCMV-Luc) on an agarose gel in the presence of increasing concentrations of polymer 1.

Figure 3:
FIG. 3 shows the retardation of pCMV-Luc DNA by polymer 1 in agarose gel electrophoresis. Each lane corresponds to a different DNA/polymer weight ratio. The ratios are as follows: 1) 1:0 (DNA only); 2) 1:0.5; 3) 1:1; 4) 1:2; 5) 1:3; 6) 1:4; 7) 1:5; 8) 1:6; 9) 1:7; and 10) 1:8.

As shown in FIG. 3, retardation of DNA migration begins at DNA/1 ratios as low as 1:0.5 (w/w) and migration is completely retarded at DNA/polymer ratios above 1:1.0 (w/w) (DNA/polymer weight ratios rather than DNA/polymer charge ratios are reported here. Although both conventions are used in the literature, we find weight ratios to be more practical and universal, since the overall charge on a polyamine is subject to environmental variations in pH and temperature. While DNA/polymer charge ratios are descriptive for polymers such as poly(lysine), they are less meaningful for polymers such as PEI and 1–3 which incorporate less basic amines.). Polymers 2 and 3 completely inhibit the migration of plasmid DNA at DNA/polymer ratios (w/w) above 1:10 and 1:1.5, respectively (data not shown). These results vary markedly from gel retardation experiments conducted using model "monomers." Since the true monomers and the degradation products of polymers 1–3 do not adequately represent the repeat units of the polymers, we used bis(methyl ester)s 4b–6b to examine the extent to which the polyvalency and cooperative binding of polycations 1–3 is necessary to achieve DNA immobilization. "Monomers" 4b–6b did not inhibit the migration of DNA at DNA/"monomer" ratios (w/w) of up to 1:30 (data not shown).

The reasons for the less-efficient complexation employing polymer 2 in the above gel electrophoresis assays most likely results from differences in the $pK_a$ values of the amines in these polymers. The direct measurement of the $pK_a$ values of polymers 1–3 is complicated by their degradability. However, we predict the range of $pK_a$ values of the amines in polymers 1 and 2 to extend from approximately 4.5 and 8.0 for polymer 1, to 3.0 and 7.0 for polymer 2, based on comparisons to structurally related poly($\beta$-amino amides) (The $pK_a$ values of structurally-related poly($\beta$-amino amides) containing piperazine and dimethylethylene diamine units in their backbones have been reported. Barbucci et al. *Polymer* 21:81–85, 1980; Barbucci et al. *Polymer* 19:1329–1334, 1978; Barbucci et al. *Macromolecules* 14:1203–1209, 1981; each of which is incorporated herein by reference). As a result, polymer 2 should be protonated to a lesser extent than polymer 1 at physiological or near-neutral pH, and would therefore be a less effective DNA condensing agent. The range of $pK_a$ values for polymer 3 should be higher than the range for polymers 1 and 2 due to the increased distance between the nitrogen atoms. Accordingly, polymer 3 forms complexes with DNA at substantially reduced concentrations relative to polymer 2.

Agarose gel retardation assays are useful in determining the extent to which polycations interact with DNA. To be useful transfection agents, however, polycations must also be able to self-assemble plasmid DNA into polymer/DNA complexes small enough to enter a cell through endocytosis. For most cell types, this size requirement is on the order of 200 nm or less (Zauner et al. *Adv. Drug Del. Rev.* 30:97–113, 1998; incorporated herein by reference), although larger particles can also be accomodated (Demeneix et al., in *Artificial Self-Assembling Systems for Gene Delivery* (Felgner et al., Eds.), American Chemical Society, Washington, D.C., 1996, pp. 146–151; Kabanov et al., in *Self-Assembling Complexes for Gene Delivery: From Laboratory to Clinical Trial*, John Wiley and Sons, New York, 1998; each of which is incorporated herein by reference). The ability of polymers 1–3 to compact plasmid DNA into nanometer-sized structures was determined by quasi-elastic laser light scattering (QELS), and the relative surface charges of the resulting complexes were quantified through $\zeta$-potential measurements. DNA/polymer particles used for particle sizing and $\zeta$-potential measurements were formed as described above for agarose gel electrophoresis assays and diluted in 20 mM HEPES buffer (pH=7.0) for analysis, as described in the Experimental Section.

Polymer 1 formed complexes with diameters ranging from 90–150 nm at DNA/polymer ratios above 1:2 (w/w), and polymer 2 condensed DNA into particles on the order of 60–125 nm at DNA/polymer ratios above 1:10. These results are consistent with the data obtained from agarose gel electrophoresis experiments above. However, the particles in these experiments aggregated over a period of hours to yield larger complexes with diameters in the range of 1–2 microns. The tendency of these particles to aggregate can be rationalized by the low $\zeta$-potentials of the DNA/polymer particles observed under these conditions. For example, complexes formed from polymer 1 at DNA/polymer ratios above 1:10 had average $\zeta$-potentials of +4.51 (±0.50) mV. The $\zeta$-potentials of complexes formed from polymer 2 at DNA/polymer ratios above 1:20 were lower, reaching a limiting value of +1.04 (±0.57) mV. These differences correlate with the estimated $pK_a$ values for these polymers, as the surfaces of particles formed from polymer 1 would be expected to slightly more protonated than particles formed from polymer 2 at pH=7.0.

Figure 4:
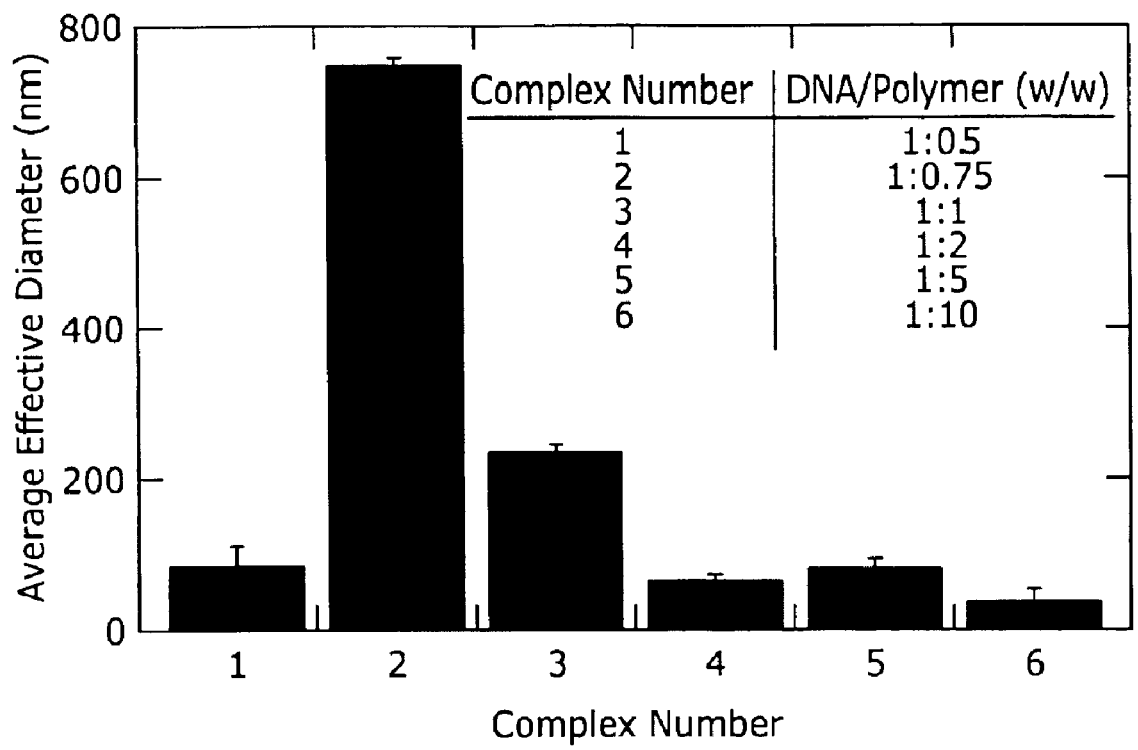
FIG. 4 shows the average effective diameters of DNA/polymer complexes formed from pCMV-Luc plasmid and polymer 3 ($M_n$=31,000) as a function of polymer concentration.

Polymer 3 formed complexes with diameters in the range of 50–150 nm at DNA/polymer ratios above 1:2. As a representative example, FIG. 4 shows the average effective diameters of particles formed with polymer 3 as a function of polymer concentration. The diameters of the particles varied within the above range from experiment to experiment under otherwise identical conditions, possibly due to subtle differences during the stirring or addition of DNA solutions during complex formation (The order of addition of polymer and DNA solutions had considerable impact on the nature of the resulting DNA/polymer complexes. In order to form small particles, for example, it was necessary to add the DNA solution to a vortexing solution of polymer. For cases in which polymer solutions were added to DNA, only large micron-sized aggregates were observed. Thus, it is possible that subtle differences in stirring or rate of addition could be responsible for variation in particle size). The $\zeta$-potentials for complexes formed from polymer 3 were on the order of +10 to +15 mV at DNA/polymer ratios above 1:1, and the complexes did not aggregate extensively over an 18 hour period (pH=7, 25° C.) The positive $\zeta$-potentials of these complexes may be significant beyond the context of particle stability, as net positive charges on particle surfaces may play a role in triggering endocytosis (Kabanov et al. *Bioconjugate Chem.* 6:7–20, 1995; Lim et al. *J. Am. Chem. Soc.* 122:6524–6525, 2000; Behr *Chimia* 51:34–36, 1997; Demeneix et al., in *Artificial Self-Assembling Systems for Gene Delivery* (Felgner et al., Eds.), American Chemical Society, Washington, D.C., 1996, pp. 146–151; Kabanov et al., in *Self-Assembling Complexes for Gene Delivery: From Laboratory to Clinical Trial*, John Wiley and Sons, New York, 1998; each of which is incorporated herein by reference).

Particles formed from polymer 3 were also relatively stable at 37° C. For example, a sample of DNA/3 (DNA/3=1:5, average diameter=83 nm) was incubated at 37° C. for 4 hours. After 4 hours, a bimodal distribution was observed consisting of a fraction averaging 78 nm (>98% by number, 70% by volume) and a fraction of larger aggregates with average diameters of approximately 2.6 microns. These results suggest that the degradation of complexes formed from polymer 3 occurred more slowly than the degradation of polymer in solution, or that partial degradation did not significantly affect the stability of the particles. The apparently increased stability of DNA/polymer complexes formed from degradable polycations relative to the degradation of the polymers in solution has also been observed for DNA/polymer complexes formed from poly(4-hydroxy-L-proline ester) (Lim et al. *J. Am. Chem. Soc.* 121:5633–5639, 1999; incorporated herein by reference).

Figure 5:
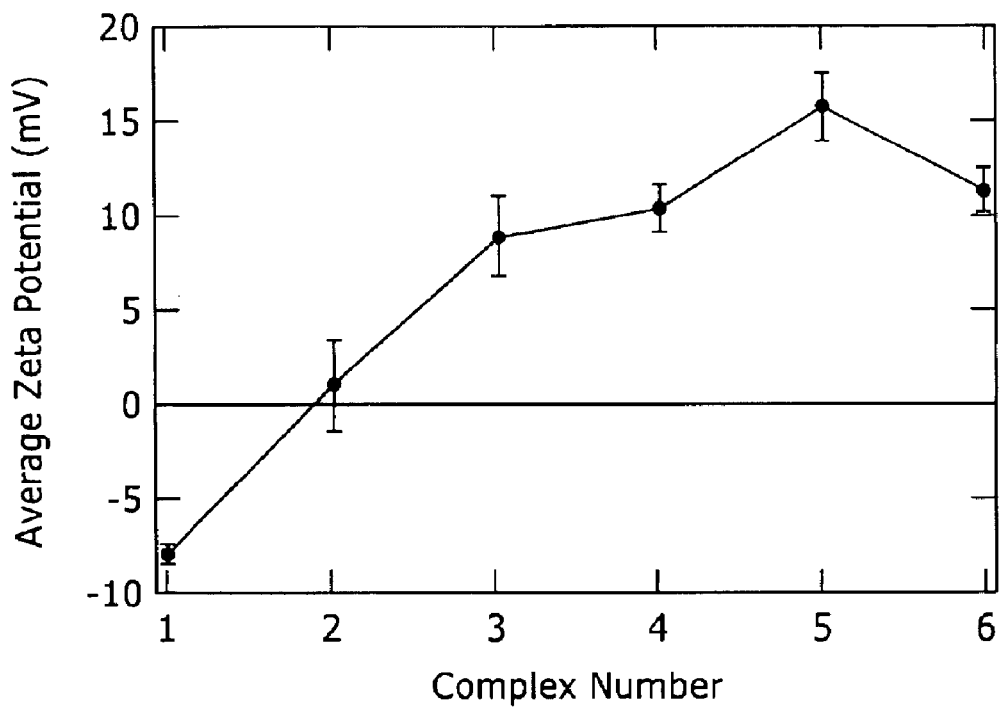
FIG. 5 shows average ζ-potentials of DNA/polymer complexes formed from pCMV-Luc plasmid and polymer 3 ($M_n$=31,000) as a function of polymer concentration. The numbers for each complex correspond to the complex numbers in FIG. 4.

The particle size and $\zeta$-potential data in FIGS. 4 and 5 are consistent with models of DNA condensation observed with other polycations (Kabanov et al. *Bioconjugate Cem.* 6:7–20, 1995; Putnam et al. *Macromolecules* 32:3658–3662, 1999; Lim et al. *J. Am. Chem. Soc.* 121:5633–5639, 1999; Lim et al. *J. Am. Chem. Soc.* 122:6524–6525, 2000; Gonzalez et al. *Bioconjugate Chem.* 10:1068–1074, 1999; each of which is incorporated herein by reference). DNA is compacted into small negatively charged particles at very low polymer concentrations and particle sizes increase with increasing polymer concentration (Accurate light scattering data could not be obtained for DNA alone or for DNA/polymer associated species at DNA/polymer ratios lower than 1:0.5, since flexible, uncondensed DNA does not scatter light as extensively as compacted DNA (Kabanov et al., in *Self-Assembling for Gene Delivery: From Laboratory to Clinical Trial*, John Wiley and Sons, New York, 1998; incorporated herein by reference).). Complexes reach a maximum diameter as charge neutrality is achieved and aggregation occurs. Particle sizes decrease sharply at DNA/polymer concentrations above charge neutrality up to ratios at which additional polymer does not contribute to a reduction in particle diameter. This model is confirmed by ζ-potential measurements made on complexes formed from these polymers. As shown in FIG. 5, the ζ-potentials of polymer/DNA particles formed from polymer 3 were negative at low polymer concentrations and charge neutrality was achieved near DNA/polymer ratios of 1:0.75, resulting in extensive aggregation. The ζ-potentials of the particles approached a limiting value ranging from +10 to +15 mV at DNA/polymer ratios above 1:2.

The average diameters of the complexes described above fall within the general size requirements for cellular endocytosis. We have initiated transfection experiments employing the NIH 3T3 cell line and the luciferase reporter gene (pCMW-Luc). Thus far, polymers 1 and 2 have shown no transfection activity in initial screening assays. By contrast, polymer 3 has demonstrated transfection efficiencies exceeding those of PEI under certain conditions. Transfection experiments were performed according to the following general protocol: Cells were grown in 6-well plates at an initial seeding density of 100,000 cells/well in 2 mL of growth medium. Cells were grown for 24 hours after which the growth medium was removed and replaced with 2 mL of serum-free medium. DNA/polymer complexes were formed as described in the Experimental Section (2 μg DNA, DNA/3=1:2 (w/w), 100 μL in MES (pH=6.0)] and added to each well. DNA/PEI complexes were formed at a weight ratio of 1:0.75, a ratio generally found in our laboratory to be optimal for PEI transfections. Transfections were carried out in serum-free medium for 4 hours, after which medium was replaced with growth medium for 20 additional hours. Relative transfection efficiencies were determined using luciferase (Promega) and cell protein assay (Pierce) kits. Results are expressed as relative light units (RLU) per mg of total cell protein: for complexes of polymer 3, 1.07 (±0.43)× $10^6$ RLU/mg; for PEI complexes, 8.07 (±0.16)×$10^5$ RLU/mg). No luciferase expression was detected for control experiments employing naked DNA or performed in the absence of DNA. These transfection data are the results of initial screening experiments. These data suggest that polymers of this general structure hold promise as synthetic vectors for gene delivery and are interesting candidates for further study. The relative efficacy of polymer 3 relative to PEI is interesting, as our initial screening experiments were performed in the absence of chloroquine and polymer 3 does not currently incorporate an obvious means of facilitating endosomal escape. It should be noted, however, that the $pK_a$ values of the amines in these polymers can be "tuned" to fall more directly within the range of physiologically relevant pH using this modular synthetic approach. Therefore, it will be possible to further engineer the "proton sponge" character (Behr *Chimia* 51:34–36, 1997; Demeneix et al., in *Artificial Self-Assembling Systems for Gene Delivery* (Felgner et al., Eds.), American Chemical Society, Washington, D.C., 1996, pp. 146–151; Kabanov et al., in *Self-Assembling Complexes for Gene Delivery: From Laboratory to Clinical Trial*, John Wiley and Sons, New York, 1998; each of which is incorporated herein by reference) of these polymers, and thus enhance their transfection efficacies, directly through the incorporation of or copolymerization with different diamine monomers.

Summary

A general strategy for the preparation of new degradable polymeric DNA transfection vectors is reported. Poly(β-amino esters) 1–3 were synthesized via the conjugate addition of N,N'-dimethylethylenediamine, piperazine, and 4,4'-trimethylenedipiperidine to 1,4-butanediol diacrylate. The amines in the bis(secondary amine) monomers actively participate in bond-forming processes during polymerization, obviating the need for amine protection/deprotection processes which characterize the synthesis of other poly(amino esters). Accordingly, this approach enables the generation of a variety of structurally diverse polyesters containing tertiary amines in their backbones in a single step from commercially available staring materials. Polymers 1–3 degraded hydrolytically in acidic and alkaline media to yield 1,4-butanediol and β-amino acids 4a–6a and the degradation kinetics were investigated at pH 5.1 and 7.4. The polymers degraded more rapidly at pH 7.4 than at pH 5.1, consistent with the pH/degradation profiles reported for other poly(amino esters). An initial screening assay designed to determine the effects of polymers 1–3 on cell growth and metabolism suggested that these polymers and their hydrolytic degradation products were non-cytotoxic relative to PEI, a non-degradable cationic polymer conventionally employed as a transfection vector.

Polymers 1–3 interacted electrostatically with plasmid DNA at physiological pH, initiating self-assembly processes that resulted in nanometer-scale DNA/polymer complexes. Agarose gel electrophoresis, quasi-elastic dynamic light scattering (QELS), and zeta potential measurements were used to determine the extent of the interactions between the oppositely charged polyelectrolytes. All three polymers were found to condense DNA into soluble DNA/polymer particles on the order of 50–200 nm. Particles formed from polymers 1 and 2 aggregated extensively, while particles formed from polymer 3 exhibited positive ζ-potentials (e.g., +10 to +15 mV) and did not aggregate for up to 18 hours. The nanometer-sized dimensions and reduced cytotoxicities of these DNA/polymer complexes suggest that polymers 1–3 may be useful as degradable polymeric gene transfection vectors. A thorough understanding of structure/activity relationships existing for this class of polymer will expedite the design of safer polymer-based alternatives to viral transfection vectors for gene therapy.

Example 2

Rapid, pH-Triggered Release from Biodegradable Poly(β-Amino Ester) Microspheres within the Ranger of Intracellular pH Experimental Section Fabrication of microspheres. The optimized procedure for the fabrication of microspheres was conducted in the following general manner: An aqueous solution of rhodamine-conjugated dextran (200 μL of a 10 μg/μL solution, $M_n$ ≈70 kD) was suspended in a solution of poly-1 in $CH_2Cl_2$ (200 mg of poly-1 in 4 mL $CH_2Cl_2$, $M_n$ ≈10 kD), and the mixture was sonicated for 10 seconds to form a primary emulsion. The cloudy pink emulsion was added directly to a rapidly homogenized (5,000 rpm) solution of poly(vinyl alcohol) [50 mL, 1% PVA (w/w)] to form the secondary emulsion. The secondary emulsion was homogenized for 30 seconds before adding it to a second aqueous PVA solution [100 mL, 0.5% PVA (w/w)]. Direct analysis of the microsphere suspension using a Coulter microparticle analyzer revealed a mean particle size of approximately 5 micrometers. The secondary emulsion was stirred for 2.5 hours at room temperature, transferred to a cold room (4° C.), and stirred for an additional 30 minutes. Microspheres were isolated at 4° C. via centrifugation, resuspended in cold water, and centrifuged again to remove excess PVA. The spheres were resuspended in water (15 mL) and lyophilized to yield a pink, fluffy powder. Characterization of the lyophilized microspheres was performed by optical, fluorescence, and scanning electron microscopies as described. Zeta potential was determined using a Brookhaven Instruments ZetaPALS analyzer.

Discussion

Microparticles formed from biodegradable polymers are attractive for use as delivery devices, and a variety of polymer-based microspheres have been employed for the sustained release of therapeutic compounds (Anderson *Nature* 392(Suppl.):25–30, 1996; Friedman *Nature Med.* 2:144–147, 1996; Crystal *Science* 270:404–410, 1995; Mulligan *Science* 260:926–932, 1993; Luo et al. *Nat. Biotechnol.* 18:33–37, 2000; Behr *Acc. Chem. Res.* 26:274–278, 1993; each of which is incorporated herein by reference). However, for small-molecule-, protein-, and DNA-based therapeutics that require intracellular administration and trafficking to the cytoplasm, there is an increasing demand for new materials that facilitate triggered release in response to environmental stimuli such as pH (Zauner et al. *Adv. Drug Del. Rev.* 30:97–113, 1998; incorporated herein by reference). Following endocytosis, the pH within cellular endosomal compartments is lowered, and foreign material is degraded upon fusion with lysosomal vesicles (Kabanov et al. *Bioconjugate Chem.* 6:7–20, 1995; incorporated herein by reference). New materials that release molecular payloads upon changes in pH within the intracellular range and facilitate escape from hostile intracellular environments could have a fundamental and broad-reaching impact on the administration of hydrolytically- and/or enzymatically-labile drugs (Zauner et al. *Adv. Drug Del. Rev.* 30:97–113, 1998; Kabanov et al. *Bioconjugate Chem.* 6:7–20, 1995; each of which is incorporated herein by reference). Herein, the fabrication of pH-responsive polymer microspheres that release encapsulated contents quantitatively and essentially instantaneously upon changes in pH within the intracellular range is reported.

The synthesis of poly(β-amino ester) 1 has been described above in Example 1 (Miller *Angew. Chem. Int. Ed.* 37:1768–1785, 1998; Hope et al. *Molecular Membrane Technology* 15:1–14, 1998; Deshmukh et al. *New J. Chem.* 21:113–124, 1997; each of which is incorporated herein by reference). Poly-1 is hydrolytically degradable, was non-cytotoxic in initial screening assays, and is currently under investigation as a synthetic vector for DNA delivery in gene therapy applications. The solubility of the polymer in aqueous media is directly influenced by solution pH. Specifically, the solid, unprotonated polymer is insoluble in aqueous media in the pH range 7.0 to 7.4, and the transition between solubility and insolubility occurs at a pH around 6.5. Based on the differences between extracellular and endosomal pH (7.4 and 5.0–6.5, respectively), we hypothesized that microspheres formed from poly-1 might be useful for the encapsulation and triggered release of compounds within the range of intracellular pH.

The encapsulation of therapeutic compounds within polymer microspheres is often achieved employing a double emulsion process (O'Donnell et al. *Adv. Drug Delivery Rev.* 28:25–42, 1997; incorporated herein by reference). The double emulsion process is well established for the fabrication of microspheres from hydrophobic polymers such as poly(lactic-co-glycolic acid) (PLGA), a biodegradable polymer conventionally employed in the development of drug delivery devices (Anderson et al. *Adv. Drug Delivery Rev.* 28:5–24, 1997; Okada *Adv. Drug Delivery Rev.* 28:43–70, 1997; each of which is incorporated herein by reference). Preliminary experiments demonstrated the feasibility of the double emulsion process for the encapsulation of water-soluble compounds using poly-1. Rhodamine-conjugated dextran was chosen as a model for subsequent encapsulation and release studies for several reasons: 1) rhodamine is fluorescent, allowing loading and release profiles to be determined by fluorescence spectroscopy, 2) loaded microspheres could be imaged directly by fluorescence microscopy, and 3) the fluorescence intensity of rhodamine is relatively unaffected by pH within the physiological range (Haugland, *Handbook of Fluorescent Probes and Research Chemicals*, 6th ed., Molecular Probes, Inc., 1996, p. 29; incorporated herein by reference).

Microspheres encapsulating labeled dextran were fabricated from poly-1 and compared to controls formed from PLGA. The size distributions of microspheres formed from poly-1 correlated well with the distributions of PLGA microspheres within the range of 5–30 µm. Average particle sizes could be controlled by variations in experimental parameters such as homogenization rates and aqueous/organic solvent ratios (O'Donnell et al. *Adv. Drug Delivery Rev.* 28:25–42, 1997; incorporated herein by reference). In contrast to PLGA microspheres, however, spheres formed from poly-1 aggregated extensively during centrifugation and washing steps (see Experimental Section above). Microspheres resuspended at pH 7.4 consisted primarily of large aggregates, and scanning electron microscopy (SEM) images revealed clusters of spheres that appeared to be physically joined or "welded" (data not shown).

Figure 6:
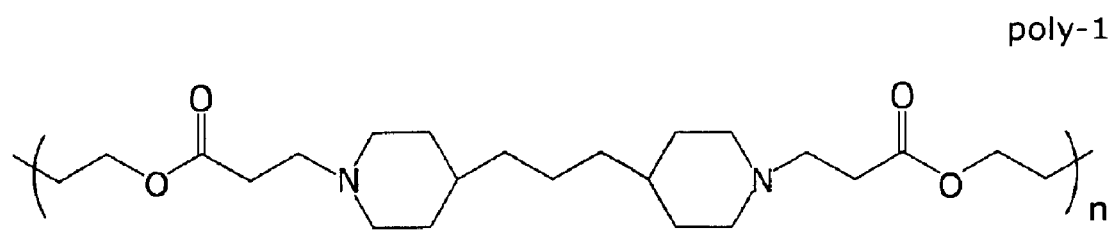
FIG. 6 is an SEM image of rhodamine/dextran-loaded microspheres fabricated from polymer 1.
Figure 6:
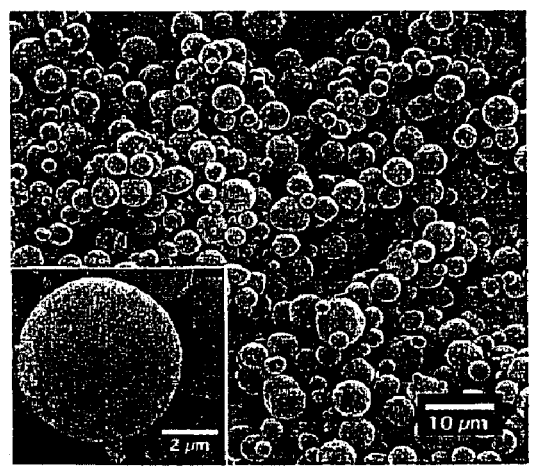
Figure 6:
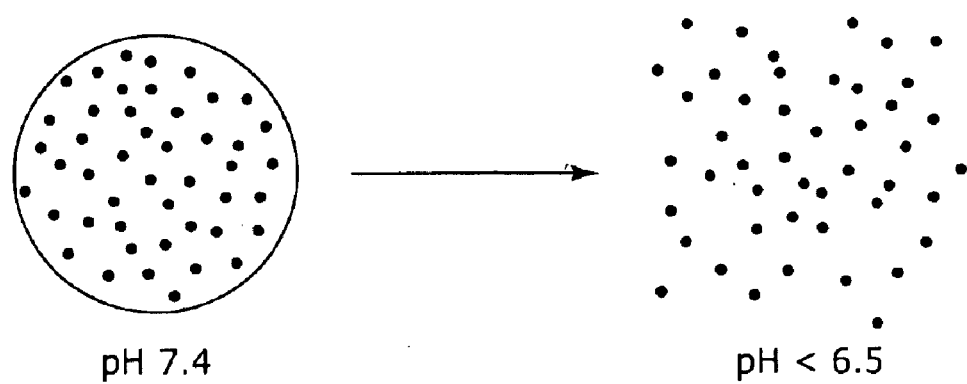

It was found that aggregation could be eliminated if centrifugation and washing were conducted at reduced temperatures (4° C.), presumably due to the hardening of the polymer spheres at this lower temperature. SEM images of dextran-loaded poly-1 microspheres prepared in the 8–10 µm range revealed significant fracturing and the formation of large holes on their surfaces. Microspheres targeted in the range of 4–6 µm, however, were essentially free of cracks, holes, and other defects (FIG. 6). Microspheres formulated for subsequent release experiments were fabricated in the smaller (<6 µm) range. Encapsulation efficiencies for loaded poly-1 microspheres, determined by dissolving the spheres at pH 5.1 and measuring fluorescence intensity, were as high as 53%.

Suspensions of dried poly-1 microspheres at pH=7.4 consisted primarily of single, isolated microspheres as determined by optical and fluorescence microscopy (FIG. 8a). The zeta potential ($\zeta$) of microparticle suspensions of poly-1 microspheres at pH 7 was +3.75 (±0.62) mV, suggesting that the surfaces of the microspheres carry an overall positive charge at physiological pH. This could be relevant to the targeting of these microspheres for cellular uptake, because net positive charges on particle surfaces may play a role in triggering endocytosis (Zauner et al. *Adv. Drug Delivery Rev.* 30:97–113, 1998; incorporated herein by reference).

Poly-1 microspheres suspended at pH 7.4 remained stable toward aggregation and degradation for several weeks (by visual inspection), but the microspheres dissolved instantly when the pH of the suspending medium was lowered between 5.1 and 6.5.

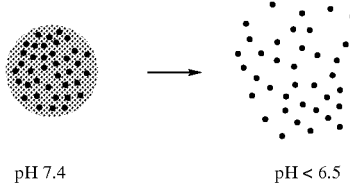

pH 7.4          pH < 6.5

The release of labeled dextran from poly-1 microspheres was determined quantitatively by fluorescence microscopy (FIG. 7). The release profile at pH 7.4 was characterized by a small initial burst in fluorescence (7–8%) which reached a limiting value of about 15% after 48 hours. This experiment demonstrated that the degradation of poly-1 was relatively slow under these conditions and that greater than 90% of encapsulated material could be retained in the polymer matrix for suitably long periods of time at physiological pH.

To examine the application of poly-1 microspheres to the triggered release of encapsulated drugs in the endosomal pH range, we conducted a similar experiment in which the pH of the suspension medium was changed from 7.4 to 5.1 during the course of the experiment. As shown in FIG. 7, the microspheres dissolved rapidly when the suspension buffer was exchanged with acetate buffer (0.1 M, pH=5.1), resulting in essentially instantaneous and quantitative release of the labeled dextran remaining in the polymer matrices. In sharp contrast, the release from dextran-loaded PLGA microspheres did not increase for up to 24 hours after the pH of the suspending medium was lowered (FIG. 7). FIG. 8 shows fluorescence microscopy images of: (a) a sample of dextran-loaded microspheres at pH 7.4; and (b) a sample to which a drop of acetate buffer was added at the upper right edge of the microscope coverslip. The rapid release of rhodamine-conjugated dextran was visualized as streaking extending from the dissolving microspheres in the direction of the diffusion of added acid and an overall increase in background fluorescence (elapsed time≈5 seconds).

When targeting therapeutic compounds for intracellular delivery via endocytosis or phagocytosis, it is not only important to consider a means by which the drug can be released from its carrier, but also a means by which the drug can escape endosomal compartments prior to being routed to lysosomal vesicles (Luo et al. *Nat. Biotechnol.* 18:33–37, 2000; Zauner et al. *Adv. Drug Delivery Rev.* 30:97–113, 1998; each of which is incorporated herein by reference). One strategy for facilitating endosomal escape is the incorporation of weak bases, or "proton sponges," which are believed to buffer the acidic environment within an endosome and disrupt endosomal membranes by increasing the internal osmotic pressure within the vesicle (Demeneix et al., in *Artificial Self-Assembling Systems for Gene Delivery* (Felgner et al., Eds.), American Chemical Society, Washington, D.C., 1996, pp. 146–151; incorporated herein by reference). Poly-1 microspheres are capable of releasing encapsulated material in the endosomal pH range via a mechanism (dissolution) that involves the protonation of amines in the polymer matrix. Thus, in addition to the rapid release of drug, poly-1 microspheres may also provide a membrane-disrupting means of endosomal escape, enhancing efficacy by prolonging the lifetimes of hydrolytically unstable drugs contained in the polymer matrix.

Microspheres fabricated from poly-1 could represent an important addition to the arsenal of pH-responsive materials applied for intracellular drug delivery, such as pH-responsive polymer/liposome formulations (Gerasimov et al. *Adv. Drug Delivery Rev.* 38:317–338, 1999; Linhart et al. *Langmuir* 16:122–127, 2000; Linhardt et al. *Macromolecules* 32:4457–4459, 1999; each of which is incorporated herein by reference). In contrast to many liposomal formulations, polymer microspheres are physically robust and can be stored dried for extended periods without deformation, decomposition, or degradation (Okada *Adv. Drug Delivery Rev.* 28:43–70, 1997; incorporated herein by reference)—an important consideration for the formulation and packaging of new therapeutic delivery systems. The microspheres investigated in this current study fall within the size range of particles commonly used to target delivery to macrophages (Hanes et al. *Adv. Drug Delivery Rev.* 28:97–119, 1997; incorporated herein by reference). The rapid pH-release profiles for the poly-1 microspheres described above may therefore be useful in the design of new DNA-based vaccines which currently employ PLGA as an encapsulating material (Singh et al. *Proc. Natl. Acad. Sci. USA* 97:811–816, 2000; Andoet al. *J. Pharm. Sci.* 88:126–130, 1999; Hedley et al. *Nat. Med.* 4:365–368, 1998; each of which is incorporated herein by reference).

Example 3

Accelerated Discovery of Synthetic Transfection Vectors: Parallel Synthesis and Screening of a Degradable Polymer Library Introduction The safe and efficient delivery of therapeutic DNA to cells represents a fundamental obstacle to the clinical success of gene therapy (Luo et al. *Nat. Biotechnol.* 18:33–37, 2000; Anderson *Nature* 392 Suppl.:25–30, 1996; each of which is incorporated herein by reference). The challenges facing synthetic delivery vectors are particularly clear, as both cationic polymers and liposomes are less effective at mediating gene transfer than viral vectors. The incorporation of new design criteria has led to recent advances toward functional delivery systems (Lim et al. *J. Am. Chem. Soc.* 123:2460–2461, 2001; Lim et al. *J. Am. Chem. Soc.* 122:6524–6525, 2000; Hwang et al. *Bioconjugate Chem.* 12:280–290, 2001; Putnam et al. *Proc. Natl. Acad. Sci. USA* 98:1200–1205, 2001; Benns et al. *Bioconjugate Chem.* 11:637–645, 2000; Midoux et al. *Bioconjugate Chem.* 10:406–411,1999; each of which is incorporated herein by reference). However, the paradigm for the development of polymeric gene delivery vectors remains the incorporation of these design elements into materials as part of an iterative, linear process-an effective, albeit slow, approach to the discovery of new vectors. Herein, we report a parallel approach suitable for the synthesis of large libraries of degradable cationic polymers and oligomers and the discovery of new synthetic vector families through rapid cell-based screening assays (for a report on the parallel synthesis and screening of degradable polymers for tissue engineering, see: Brocchini et al. *J. Am. Chem. Soc.* 119:4553–4554, 1997; incorporated herein by reference).

Experimental Section

General Considerations. All manipulations involving live cells or sterile materials were performed in a laminar flow hood using standard sterile technique. Gel permeation chromatography (GPC) was performed using a Hewlett Packard 1100 Series isocratic pump, a Rheodyne Model 7125 injector with a 100-µL injection loop, and two PL-Gel mixed-D columns in series (5 µm, 300×7.5 mm, Polymer Laboratories, Amherst, Mass.). THF/0.1M piperidine was used as the eluent at a flow rate of 1.0 mL/min. Data was collected using an Optilab DSP interferometric refractometer (Wyatt Technology, Santa Barbara, Calif.) and processed using the TriSEC GPC software package (Viscotek Corporation, Houston, Tex.). The molecular weights and polydispersities of the polymers are reported relative to monodisperse polystyrene standards. Materials. Primary amine and secondary amine monomers 1–20 were purchased from Aldrich Chemical Company (Milwaukee, Wis.), Lancaster (Lancashire, UK), Alfa Aesar Organics (Ward Hill, Mass.), and Fluka (Milwaukee, Wis.). Diacrylate monomers A–G were purchased from Polysciences, Inc. (Warrington, Pa.), Alfa Aesar, and Scientific Polymer Products, Inc. (Ontario, N.Y.). All monomers were purchased in the highest purity available (from 97% to 99+%) and were used as received without additional purification. Plasmid DNA containing the firefly luciferase reporter gene (pCMV-Luc) was purchased from Elim Biopharmaceuticals, Inc. (San Francisco, Calif.) and used without further purification. (3-[4,5-dimethylthiazol-2-yl]-2,5-diphenyltetrazolium bromide (MTT) was purchased from Sigma Chemical Company (St. Louis, Mo.). Monkey kidney fibroblasts (COS-7 cells) used in transfection assays were purchased from American Type Culture Collection (Manassas, Va.) and grown at 37° C., 5% $CO_2$ in Dulbecco's modified Eagle's medium, 90%; fetal bovine serum, 10%; penicillin, 100 units/mL; streptomycin, 100 µg/mL. Luciferase detection kits used in high-throughput transfection assays were purchased from Tropix (Bedford, Mass.). All other materials and solvents were used as received without additional purification.

Synthesis of Polymer Library. All 140 polymerization reactions were conducted simultaneously as an array of individually labeled vials according to the following general protocol. Individual exceptions are noted where appropriate. Amine monomers 1–20 (2.52 mmol) were charged into appropriately labeled vials (as shown below): liquid monomers were measured and transferred quantitatively using microliter pipettes; solid monomers were weighed directly into each vial. Anhydrous $CH_2Cl_2$ (1 mL) was added to each vial. One equivalent of liquid diacrylates A–F (2.52 mmol) was added to each appropriate reaction vial using a microliter pipette, and the vial was capped tightly with a Teflon-lined cap. One equivalent of semi-solid diacrylate G was added to the appropriate vials as a solution in $CH_2Cl_2$ (2.52 mmol, 1 mL of a 2.52M solution in $CH_2Cl_2$) and the vials were tightly capped. An additional aliquot of $CH_2Cl_2$ (2 mL) was added to the reaction vials containing 19 and 20 to aid in the solubility of these monomers. The tightly capped vials were arrayed in two plastic test tube racks and secured to an orbital shaker in a 45° C. oven. (CAUTION: The heating of capped vials represents a possible explosion hazard. Oven temperature was monitored periodically for one week prior to the experiment to ensure reliable thermal stability. Temperatures were found to vary within +/−1° C. during this time period. Several test vials were monitored prior to conducting the larger experiment). The reaction vials were shaken vigorously at 45° C. for 5 days and allowed to cool to room temperature. Vials were placed in a large dessicator and placed under aspirator vacuum for 1 day and high vacuum for an additional 5 days to ensure complete removal of solvent. The samples obtained were analyzed by GPC (55% of total library, see Table 2) and used directly in all subsequent screening experiments.

TABLE 2

GPC survey of 55% of the screening library showing molecular weights ($M_w$) and polydispersities (shown in parentheses).

|    | A      | B      | C      | D      | E      | F      | G      |
|----|--------|--------|--------|--------|--------|--------|--------|
| 1  | 5900   | 4725   |        |        | 5220   | 1690   |        |
|    | (1.93) | (1.89) |        |        | (1.95) | (1.74) |        |
| 2  | 6920   | 6050   |        |        | 5640   |        |        |
|    | (1.87) | (1.78) |        |        | (1.85) |        |        |
| 3  | 6690   | 6050   |        |        |        |        | 2060   |
|    | (1.79) | (1.78) |        |        |        |        | (1.76) |
| 4  | 7810   | 5720   | 9720   | 7960   | 7940   |        |        |
|    | (2.49) | (2.20) | (2.49) | (4.08) | (3.25) |        |        |
| 5  | 10 800 | 5000   | 15 300 | 17 200 | 15 300 | Insol. | 9170   |
|    | (2.75) | (2.50) | (3.17) | (6.91) | (3.92) |        | (2.50) |
| 6  | 21 000 | 10 200 |        | 18 000 |        |        |        |
|    | (3.70) | (3.4)  |        | (6.06) |        |        |        |
| 7  | 14 300 | 11 880 | 20 200 | 10 300 | 15 500 |        | 22 500 |
|    | (3.25) | (3.3)  | (3.44) | (4.26) | (4.89) |        | (3.92) |
| 8  | 2310   | 11 520 |        | 2230   |        |        |        |
|    | (1.62) | (3.60) |        | (1.73) |        |        |        |
| 9  | 1010   | 2505   | 1240   |        |        | Insol. |        |
|    | (1.33) | (1.67) | (1.16) |        |        |        |        |
| 10 |        | <1000  | Insol. |        |        |        |        |
| 11 | 6800   | Insol. | 9440   | 5550   | 6830   | 1990   | 6420   |
|    | (1.91) |        | (1.79) | (2.23) | (1.93) | (1.43) | (1.75) |
| 12 | 9310   | 9100   | 11 900 | 5810   |        |        | 12 300 |
|    | (2.06) | (2.53) | (2.18) | (1.77) |        |        | (1.85) |
| 13 | 2990   | 3180   | 3680   | 2550   | 3230   |        | 3580   |
|    | (1.64) | (2.12) | (1.64) | (1.82) | (1.82) |        | (1.64) |
| 14 | 1350   | 3180   | 2110   | 1400   | 1752   |        | 2025   |
|    | (1.35) | (2.12) | (1.69) | (1.4)  | (1.46) |        | (1.62) |
| 15 |        | 1550   |        |        |        |        |        |
|    |        | (1.51) |        |        |        |        |        |
| 16 |        | 16 380 |        |        |        |        |        |
|    |        | (2.60) |        |        |        |        |        |
| 17 |        | 8520   |        | 7290   |        |        |        |
|    |        | (2.13) |        | (1.94) |        |        |        |
| 18 |        | <1000  |        |        |        |        |        |
| 19 | 12 400 | 18 445 | 39 700 | 17 400 | 14 800 |        | 13 900 |
|    | (2.28) | (2.17) | (1.90) | (1.93) | (1.98) |        | (1.86) |
| 20 | 16 900 | 46 060 | 49 600 | 30 700 | 18 700 |        | 17 100 |
|    | (2.40) | (3.29) | (2.25) | (2.72) | (2.72) |        | (2.22) |

Determination of Water Solubility. The solubilities of all samples sample were determined simultaneously at a concentration of 2 mg/mL in the following general manner. Each polymer sample (5 mg) was weighed into a 12 mL scintillation vial and 2.5 mL of acetate buffer (25 mM, pH=5.0) was added to each sample using an a pipettor. Samples were shaken vigorously at room temperature for 1 hour. Each sample was observed visually to determine solubility.

Agarose Gel Electrophoresis Assay. The agarose gel electrophoresis assay used to determine the ability of polymers to form complexes with DNA was performed in the following manner. Using the solutions prepared in the above solubility assay (2 mg/mL in acetate buffer, 25 mM, pH=5.0), stock solutions of the 70 water-soluble polymers were arrayed into a 96-well cell culture plate. DNA/polymer complexes were formed at a ratio of 1:5 (w/w) by transferring 10 µL of each polymer solution from the stock plate to a new plate using a multichannel pipettor. Each polymer was further diluted with 90 µL of acetate buffer (25 mM, pH=5.0, total volume=100 µL) and the plate was shaken for 30 seconds on a mechanical shaker. An aqueous solution of plasmid DNA (100 µL of a 0.04 µg/µL solution) was added to each well in the plate and the solutions were vigorously mixed using a multichannel pipettor and a mechanical shaker. DNA/polymer complexes were formed at a ratio of 1:20 (w/w) in the same manner with the following exceptions: 40 μL of polymer stock solution was transferred to a new plate and diluted with 60 μL of acetate buffer (total volume=100 μL) prior to adding the aqueous DNA solution (100 μL). DNA/polymer complexes were incubated at room temperature for 30 minutes, after which samples of each solution (15 μL) were loaded into a 1% agarose gel (HEPES, 20 mM, pH=7.2, 500 ng/mL ethidium bromide) using a multichannel pipettor. NOTE: Samples were loaded on the gel with a loading buffer consisting of 10% Ficoll 400 (Amersham Pharmacia Biotech, Uppsala, Sweden) in HEPES (25 mM, pH=7.2). Bromphenol blue was not included as a visual indicator in the loading buffer, since this charged dye appeared to interfere with the complexation of polymer and DNA. Samples were loaded according to the pattern shown in FIG. 9, such that samples corresponding to DNA/polymer ratios of 1:5 and 1:20 were assayed in adjacent positions on the gel. The gel was run at 90V for 30 minutes and DNA bands were visualized by ethidium bromide staining.

General Protocol for Cell Transfection Assays. Transfection assays were performed in triplicate in the following general manner. COS-7 cells were grown in 96-well plates at an initial seeding density of 15,000 cells/well in 200 μL of phenol red-free growth medium (90% Dulbecco's modified Eagle's medium, 10% fetal bovine serum, penicillin 100 units/mL, streptomycin 100 μg/mL). Cells were grown for 24 hours in an incubator, after which the growth medium was removed and replaced with 200 μL of Optimem medium (Invitrogen Corp., Carlsbad, Calif.) supplemented with HEPES (total concentration=25 mM). Polymer/DNA complexes prepared from the 56 water-soluble/DNA-complexing polymers previously identified were prepared as described above at a ratio of 1:20 (w/w)) using a commercially available plasmid containing the firefly luciferase reporter gene (pCMV-Luc). An appropriate volume of each sample was added to the cells using a multichannel pipettor (e.g., 15 μL yielded 300 ng DNA/well; 30 μL yielded 600 ng DNA/well). Controls employing poly(ethylene imine) (PEI) and polylysine, prepared at DNA/polymer ratios of 1:1, were prepared in a similar manner and included with DNA and no-DNA controls. Controls employing Lipofectamine 2000 (Invitrogen Corp.) were performed at several concentrations (0.1, 0.2, 0.4, and 0.6 μL) as described in the technical manual for this product (http://lifetechnologies.com). Cells were incubated for 4 hours, after which the serum-free growth medium was removed and replaced with 100 μL of phenol-red-free growth medium. Cells were incubated for an additional period of time (typically varied between 36 to 60 hours) and luciferase expression was determined using a commercially available assay kit (Tropix, Inc., Bedford, Mass.). Luminescence was quantified in white, solid-bottom polypropylene 96-well plates using a 96-well bioluminescence plate reader. Luminescence was expressed in relative light units and was not normalized to total cell protein in this assay.

Results and Discussion

Poly(β-amino ester)s are hydrolytically degradable, condense plasmid DNA at physiological pH, and are readily synthesized via the conjugate addition of primary or secondary amines to diacrylates (Eq. 1 and 2) (Lynn et al. *J. Am. Chem. Soc.* 122:10761–10768, 2000; incorporated herein by reference). An initial screen of model polymers identified these materials as potential gene carriers and demonstrated that structural variations could have a significant impact on DNA binding and transfection efficacies (Lynn et al. *J. Am. Chem. Soc.* 122:10761–10768, 2000; incorporated herein by reference). We reasoned that this approach provided an attractive framework for the elaboration of large libraries of structurally-unique polymers for several reasons: 1) diamine and diacrylate monomers are inexpensive, commercially available starting materials, 2) polymerization can be accomplished directly in a single synthetic step, and 3) purification steps are generally unnecessary as no byproducts are generated during polymerization.

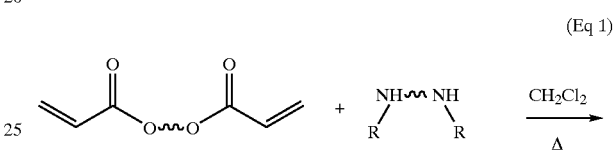
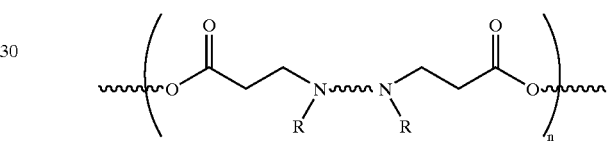

(Eq 1)

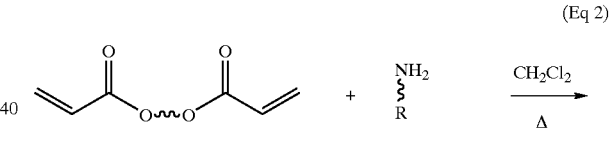
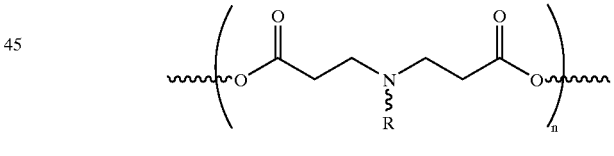

(Eq 2)

The paucity of commercially available bis(secondary amines) limits the degree of structural diversity that can be achieved using the above synthetic approach. However, the pool of useful, commercially available monomers is significantly expanded when primary amines are considered as potential library building blocks. Because the conjugate addition of amines to acrylate groups is generally tolerant of functionalities such as alcohols, ethers, and tertiary amines (Ferruti et al. *Adv. Polym. Sci.* 58:55–92, 1984; incorporated herein by reference), we believed that the incorporation of functionalized primary amine monomers into our synthetic strategy would serve to broaden structural diversity. Diacrylate monomers A–G and amine monomers 1–20 were selected for the synthesis of an initial screening library.

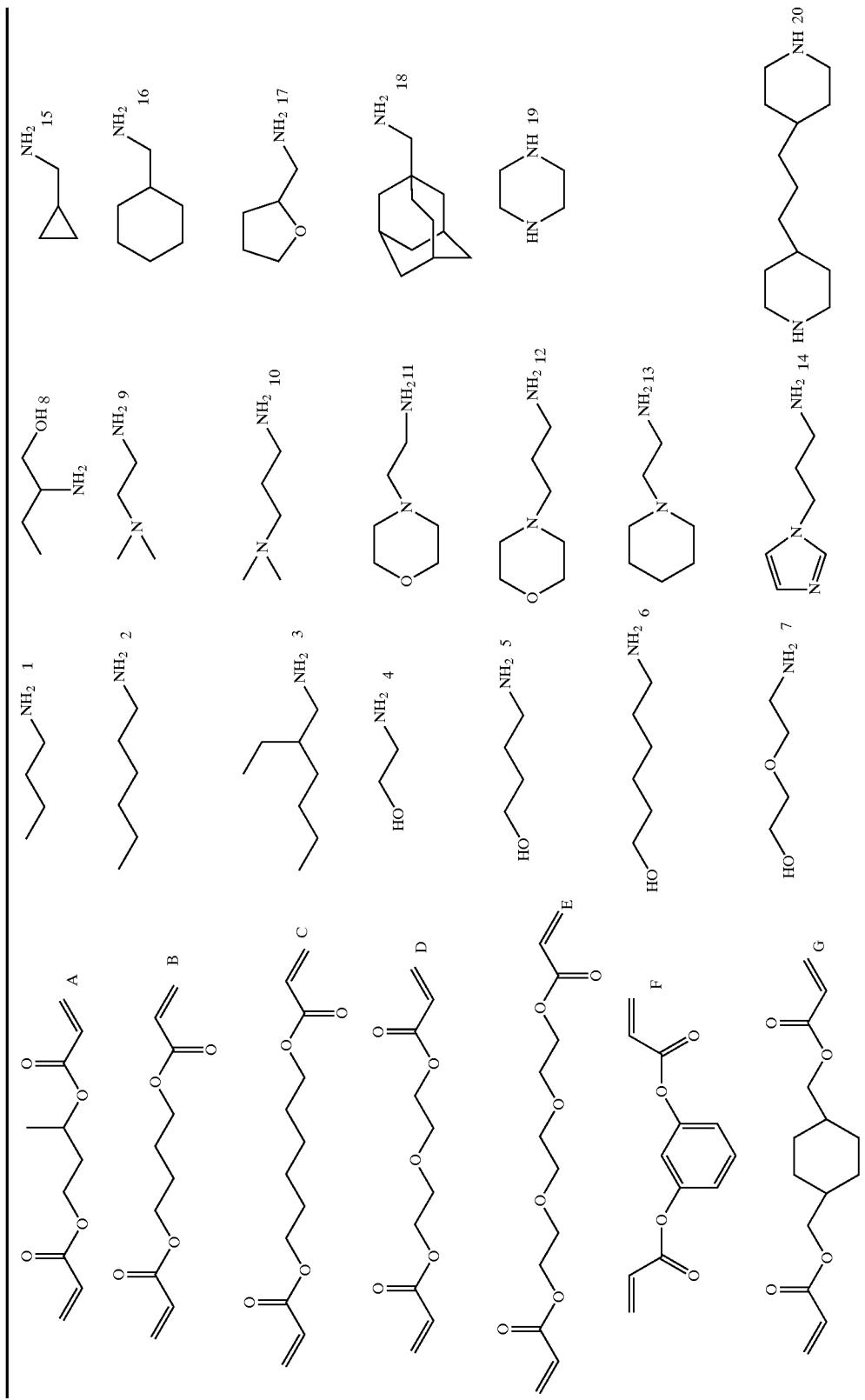

The size of the library constructed from this set of monomers (7 diacrylates×20 amines=140 structurally-unique polymers) was chosen to be large enough to incorporate sufficient diversity, yet small enough to be practical without the need for automation in our initial studies. It was unclear at the outset whether a polymer such as G16 (formed from hydrophobic and sterically bulky monomers G and 16) would be water-soluble at physiological pH or be able to condense DNA sufficiently. However, monomers of this type were deliberately incorporated to fully explore diversity space, and in anticipation that this library may ultimately be useful as a screening population for the discovery of materials for applications other than gene delivery (For a report on the parallel synthesis and screening of degradable polymers for tissue engineering, see: Brocchini et al. *J. Am. Chem. Soc.* 119:4553–4554, 1997, incorporated herein by reference; Lynn et al. *Angew. Chem. Int. Ed.* 40:1707–1710, 2001; incorporated herein by reference).

Polymerization reactions were conducted simultaneously as an array of individually labeled vials. Reactions were performed in methylene chloride at 45° C. for 5 days, and polymers were isolated by removal of solvent to yield 600–800 mg of each material. Reactions performed on this scale provided amounts of each material sufficient for routine analysis by GPC and all subsequent DNA-binding, toxicity, and transfection assays. A survey of 55% of the library by GPC indicated molecular weights ranging from 2000 to 50000 (relative to polystyrene standards). As high molecular weights are not required for DNA-complexation and transfection (as shown below) (Kabanov et al., in *Self-Assembling for Gene Delivery: From Laboratory to Clinical Trial*, John Wiley and Sons, New York, 1998; incorporated herein by reference), this library provided a collection of polymers and oligomers suitable for subsequent screening assays.

Figure 9:
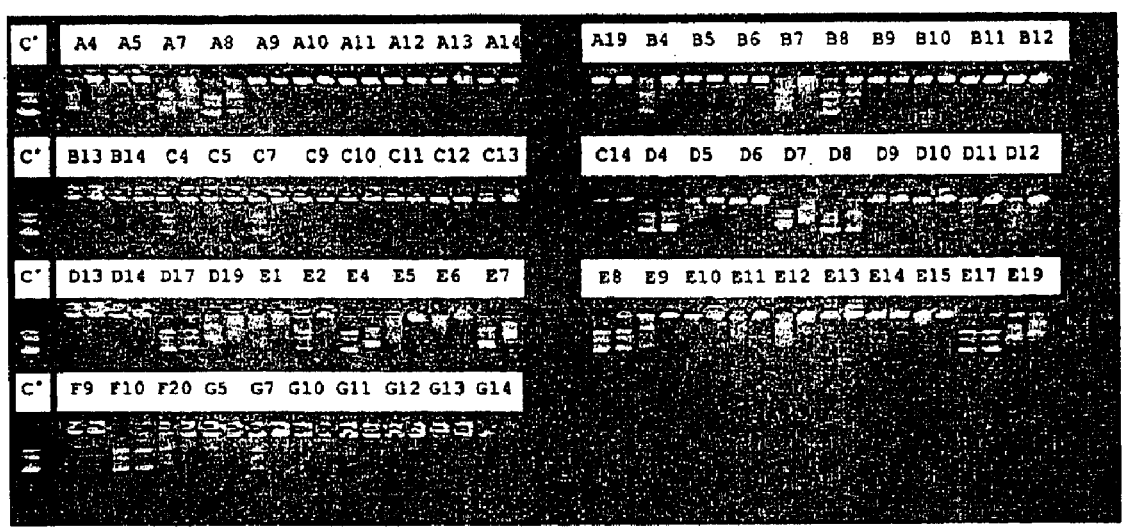
FIG. 9 demonstrates the gel electrophoresis assay used to identify DNA-complexing polymers. Lane annotations correspond to the 70 water-soluble members of the screening library. For each polymer, assays were performed at DNA/polymer ratios of 1:5 (left well) and 1:20 (right well). Lanes marked C* contain DNA alone (no polymer) and were used as a control.

Of the 140 members of the screening library, 70 samples were sufficiently water-soluble (2 mg/mL, 25 mM acetate buffer, pH=5.0) to be included in an electrophoretic DNA-binding assay (FIG. 9). To perform this assay as rapidly and efficiently as possible, samples were mixed with plasmid DNA at ratios of 1:5 and 1:20 (DNA/polymer, w/w) in 96-well plates and loaded into an agarose gel slab capable of assaying up to 500 samples using a multi-channel pipettor. All 70 water-soluble polymer samples were assayed simultaneously at two different DNA/polymer ratios in less than 30 minutes. As shown in FIG. 9, 56 of the 70 water-soluble polymer samples interacted sufficiently with DNA to retard migration through the gel matrix (e.g., A4 or A5), employing the 1:20 DNA/polymer ratio as an exclusionary criterion. Fourteen polymers were discarded from further consideration (e.g., A7 and A8), as these polymers did not complex DNA sufficiently.

Figure 10:
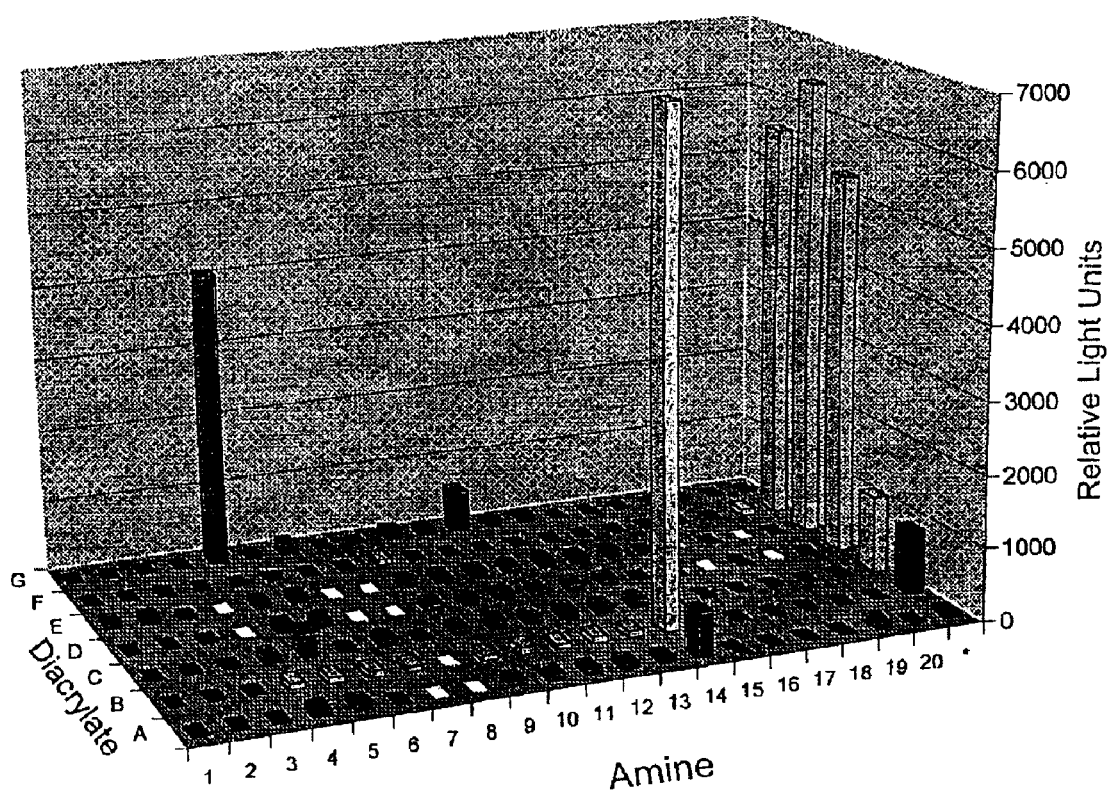
FIG. 10 shows transfection data as a function of structure for an assay employing pCMV-Luc (600 ng/well, DNA/polymer=1:20). Light units are arbitrary and not normalized to total cell protein; experiments were performed in triplicate (error bars not shown). Black squares represent water-insoluble polymers, white squares represent water-soluble polymers that did not complex DNA in FIG. 9. The right column (marked "*") displays values for the following control experiments: no polymer (green), PEI (red), and Lipofectamine (light blue).

The DNA-complexing materials identified in the above assay were further investigated in transfection assays employing plasmid DNA and the COS-7 cell line. All assays were performed simultaneously with the firefly luciferase reporter gene (pCMV-Luc) and levels of expressed protein were determined using a commercially available assay kit and a 96-well luminescence plate reader. FIG. 10 displays data generated from an assay employing pCMV-Luc (600 ng/well) at DNA/poly ratios of 1:20 (w/w). The majority of the polymers screened did not mediate transfection above a level typical of "naked" DNA (no polymer) controls under these conditions. However, several wells expressed higher levels of protein and the corresponding polymers were identified as "hits" in this assay. Polymers B14 ($M_w$=3180) and G5 ($M_w$=9170), for example, yielded transfection levels 4–8 times higher than control experiments employing poly(ethylene imine) (PEI), a polymer conventionally employed as a synthetic transfection vector (Boussif al. *Proc. Natl. Acad. Sci. USA* 92:7297–7301, 1995; incorporated herein by reference), and transfection levels within or exceeding the range of expressed protein using Lipofectamine 2000 (available from Invitrogen Corp. (Carlsbad, Calif.)), a leading commercially available lipid-based transfection vector system. Polymers A14, C5, G7, G10, and G12 were also identified as positive "hits" in the above experiment, but levels of gene expression were lower than B14 and G5.

Structural differences among synthetic polymers typically preclude a general set of optimal transfection conditions. For example, polymers C5, C14, and G14 were toxic at the higher concentrations employed above (Determined by the absence of cells in wells containing these polymers as observed upon visual inspection. These polymers were less toxic and mediated transfection at lower concentration.), but mediated transfection at lower DNA and polymer concentrations (data not shown). The assay system described above can easily be modified to evaluate polymers as a function of DNA concentration, DNA/polymer ratio, cell seeding densities, or incubation times. Additional investigation will be required to more fully evaluate the potential of this screening library, and experiments to this end are currently underway.

The assays above were performed in the absence of chloroquine, a weak base commonly added to enhance in vitro transfection (Putnam et al. *Proc. Natl. Acad. Sci. USA* 98:1200–1205, 2001; Benns et al. *Bioconjugate Chem.* 11:637–645, 2000; Midoux et al. *Bioconjugate Chem.* 10:406–411, 1999; Kabanov et al., in *Self-Assembling Complexes for Gene Delivery: From Laboratory to Clinical Trial*, John Wiley and Sons, New York, 1998; each of which is incorporated herein by reference), and the results therefore reflect the intrinsic abilities of those materials to mediate transfection. The polymers containing monomer 14 are structurally similar to other histidine containing "proton sponge" polymers (Putnam et al. *Proc. Natl. Acad. Sci. USA* 98:1200–1205, 2001; Benns et al. *Bioconjugate Chem.* 11:637–645, 2000; Midoux et al. *Bioconjugate Chem.* 10:406–411, 1999; each of which is incorporated herein by reference), and could enhance transfection by buffering acidic intracellular compartments and mediating endosomal escape (Putnam et al. *Proc. Natl. Acad. Sci. USA* 98:1200–1205, 2001; Benns et al. *Bioconjugate Chem.* 11:637–645, 2000; Midoux et al. *Bioconjugate Chem.* 10:406–411, 1999; Boussif et al. *Proc. Natl. Acad. Sci. USA* 92:7297–7301, 1995; each of which is incorporated herein by reference). The efficacy of polymers containing monomer 5 is surprising in this context, as these materials do not incorporate an obvious means of facilitating endosomal escape. While the efficacy of these latter polymers is not yet understood, their discovery helps validate our parallel approach and highlights the value of incorporating structural diversity, as these polymers may not have been discovered on an ad hoc basis. Polymers incorporating hydrophilic diacrylates D and E have not produced "hits" under any conditions thus far, providing a possible basis for the development of more focused libraries useful for the elucidation of structure/activity relationships.

We have generated a library of 140 degradable polymers and oligomers useful for the discovery of new DNA-complexing materials and gene delivery vectors. Several of these materials are capable of condensing DNA into structures small enough to be internalized by cells and release the DNA in a transcriptionally active form. The total time currently required for library design, synthesis, and initial screening assays is approximately two weeks. However, the incorporation of robotics and additional monomers could significantly accelerate the pace at which new DNA-complexing materials and competent transfection vectors are identified.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A polymer of the formula:

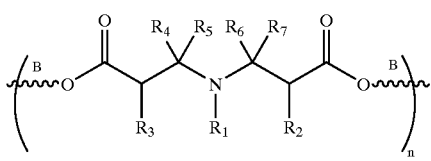

wherein:
linker B is selected from the group consisting of carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups;

$R_1$, $R_2$, $R_3$, $R_4$, $R_5$, $R_6$, and $R_7$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups; and n is an integer between 5 and 10,000.

2. A polymer of the formula:

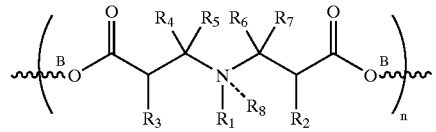

wherein: linker B is selected from the group consisting of carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups;

$R_1$, $R_2$, $R_3$, $R_4$, $R_5$, $R_6$, and $R_7$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups; $R_8$ is selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups, and the counter anion is selected from the group consisting of chloride, fluoride, bromide, iodide, sulfate, nitrate, fumarate, acetate, carbonate, stearate, laurate, and oleate; and n is an integer between 5 and 10,000.

3. The polymer of claim 2 wherein $R_8$ is hydrogen.
4. The polymer of claim 1, wherein the compound has a molecular weight between 1,000 and 100,000 g/mol.
5. The polymer of claim 1, wherein the compound has a molecular weight between 4,000 and 50,000 g/mol.
6. The polymer of claim 1, wherein the linker B is polyethylene.
7. The polymer of claim 1, wherein the linker B is polyethylene glycol.

8. The polymer of claim 1 of formula:

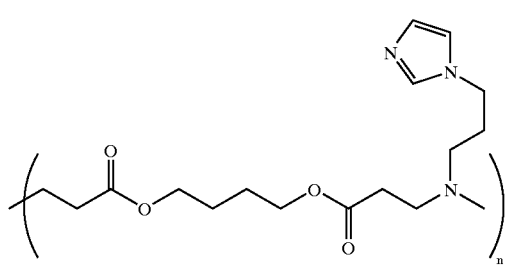
B14 wherein n is an integer between 3 and 10,000; and substituted polymers and salts thereof.

9. The polymer of claim 1 of formula:

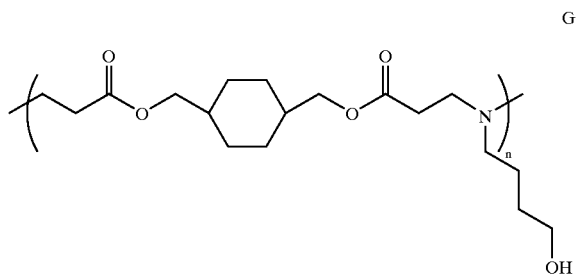
G5 wherein n is an integer between 3 and 10,000; and substituted polymers and salts thereof.

10. The polymer of claim 1 of formula:

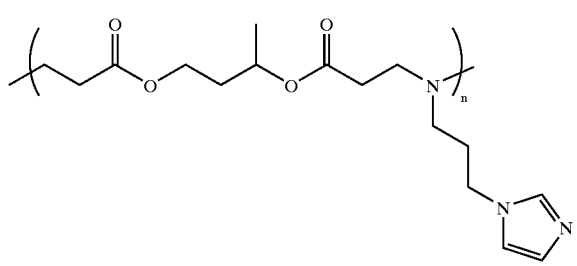
A14 wherein n is an integer between 3 and 10,000; and substituted polymers and salts thereof.

11. The polymer of claim 1 of formula:

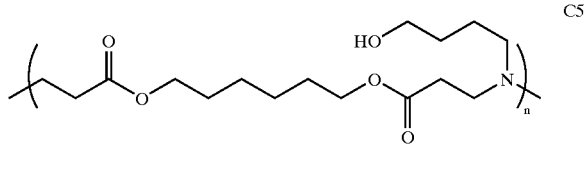
C5 wherein n is an integer between 3 and 10,000; and substituted polymers and salts thereof.

12. The polymer of claim 1 of formula:

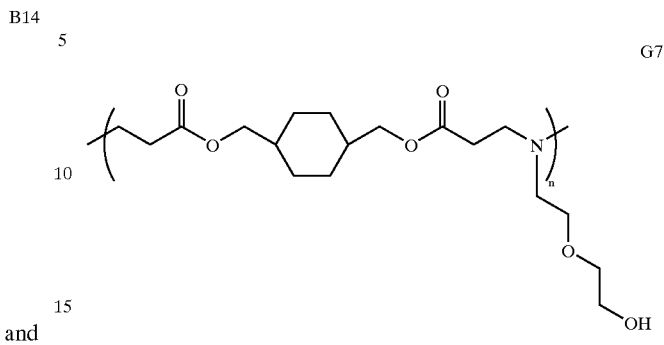
G7 wherein n is an integer between 3 and 10,000; and substituted polymers and salts thereof.

13. The polymer of claim 1 of formula:

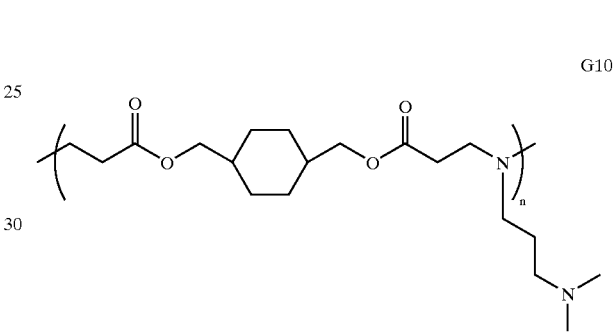
G10 wherein n is an integer between 3 and 10,000; and substituted polymers and salts thereof.

14. The polymer of claim 1 of formula:

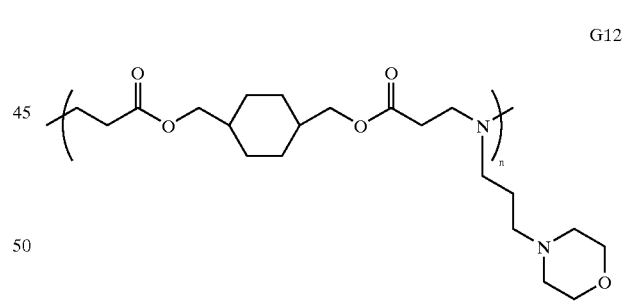
G12 wherein n is an integer between 3 and 10,000; and substituted polymers and salts thereof.

15. The polymer of claim 1 of formula:

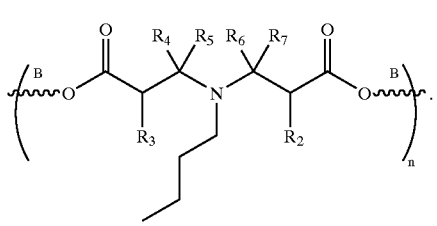

16. The polymer of claim 1 of formula:
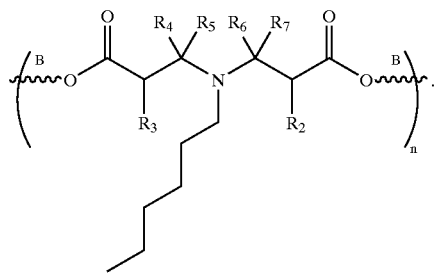
17. The polymer of claim 1 of formula:
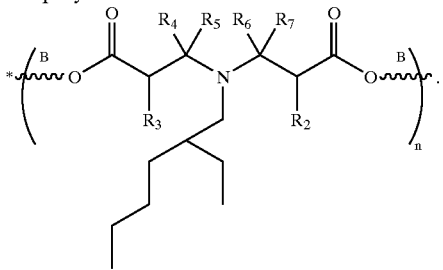
18. The polymer of claim 1 of formula:
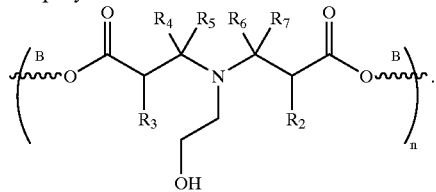
19. The polymer of claim 1 of formula:
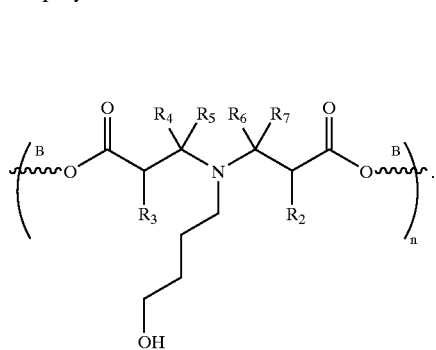
20. The polymer of claim 1 of formula:
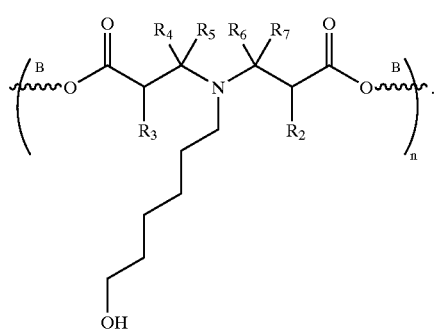
21. The polymer of claim 1 of formula:
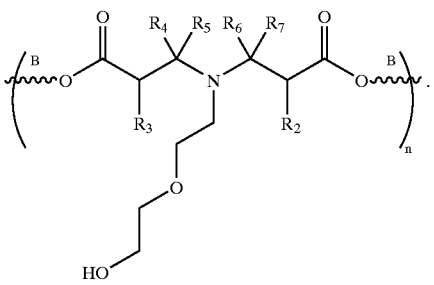
22. The polymer of claim 1 of formula:
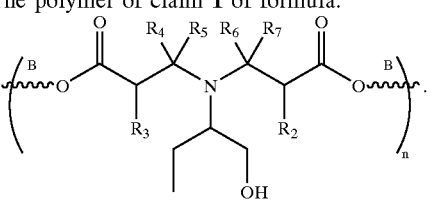
23. The polymer of claim 1 of formula:
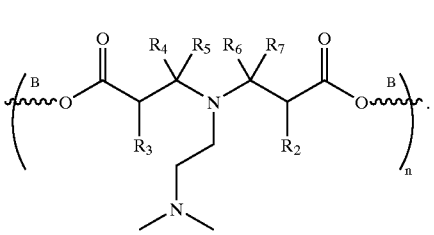
24. The polymer of claim 1 of formula:
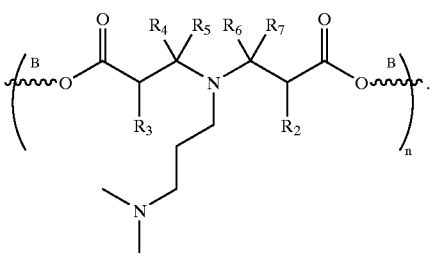
25. The polymer of claim 1 of formula:
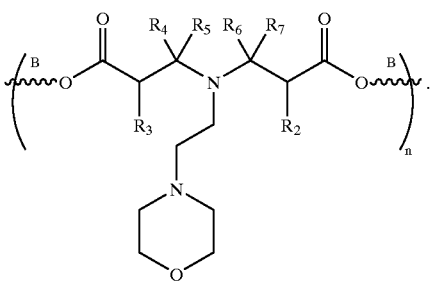

26. The polymer of claim 1 of formula:
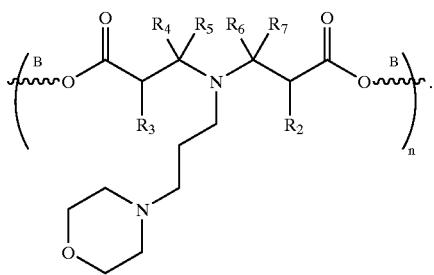
27. The polymer of claim 1 of formula:
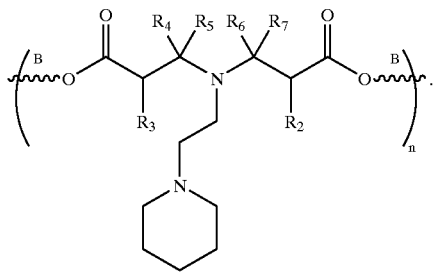
28. The polymer of claim 1 of formula:
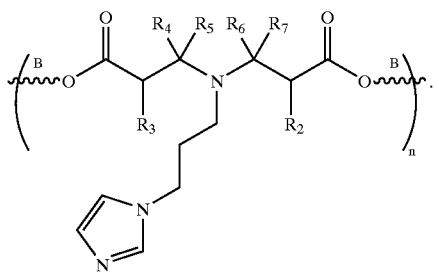
29. The polymer of claim 1 of formula:
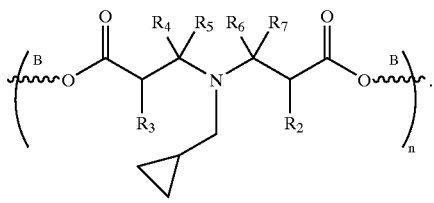
30. The polymer of claim 1 of formula:
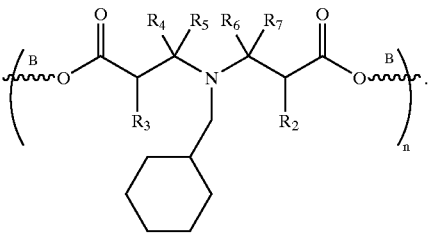
31. The polymer of claim 1 of formula:
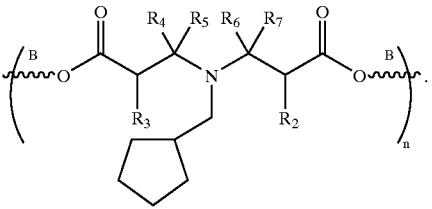
32. The polymer of claim 1 of formula:
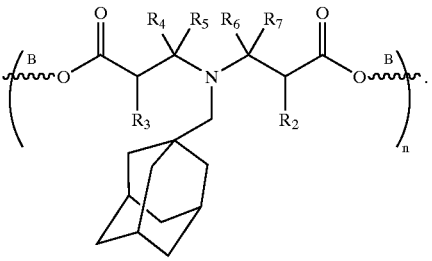
33. The polymer of claim 1 of formula:
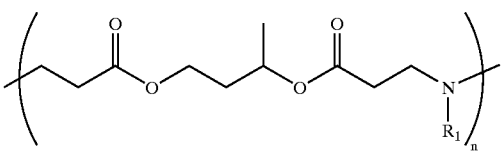
34. The polymer of claim 1 of formula:
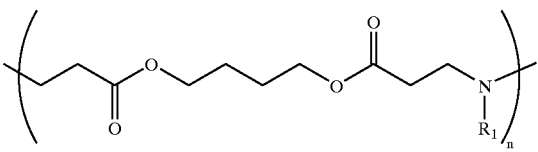
35. The polymer of claim 1 of formula:
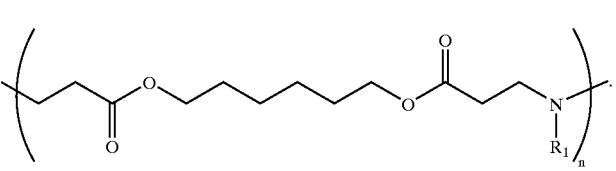

36. The polymer of claim 1 of formula:
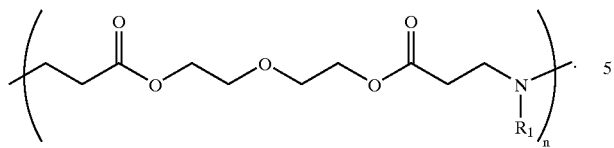
37. The polymer of claim 1 of formula:
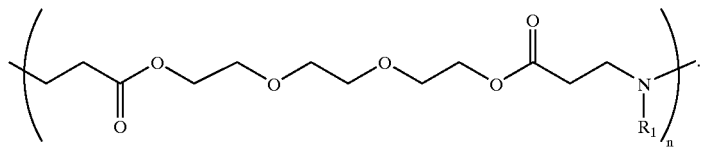
38. The polymer of claim 1 of formula:
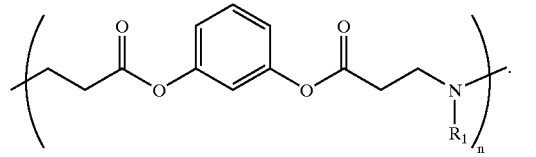
39. The polymer of claim 1 of formula:
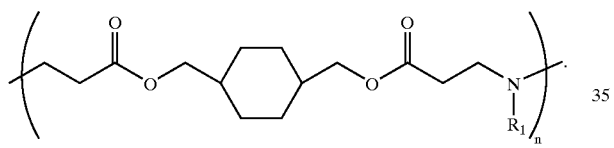
* * * * *

UNITED STATES PATENT AND TRADEMARK OFFICE
CERTIFICATE OF CORRECTION

| | | |
|---|---|---|
| PATENT NO. | : 6,998,115 B2 | Page 1 of 1 |
| APPLICATION NO. | : 09/969431 | |
| DATED | : February 14, 2006 | |
| INVENTOR(S) | : Langer et al. | |

It is certified that error appears in the above-identified patent and that said Letters Patent is hereby corrected as shown below:

On the title page (*) Notice, delete "This patent is subject to a terminal disclaimer."

Signed and Sealed this

Nineteenth Day of February, 2008

JON W. DUDAS
*Director of the United States Patent and Trademark Office*

UNITED STATES PATENT AND TRADEMARK OFFICE
CERTIFICATE OF CORRECTION

PATENT NO. : 6,998,115 B2
APPLICATION NO. : 09/969431
DATED : February 14, 2006
INVENTOR(S) : Robert S. Langer et al.

It is certified that error appears in the above-identified patent and that said Letters Patent is hereby corrected as shown below:

*In the Specification*

At column 1, lines 11-20, please replace the current "Government Support" section as shown below:

"The work described herein was supported, in part, by grants from the National Science Foundation (Cooperative Agreement #ECC9843342 to the MIT Biotechnology Process Engineering Center), the National Institutes of Health (GM26698; NRSA Fellowship # 1 F32 GM20227-01), and the Department of the Army (Cooperative Agreement # DAMD 17-99-2-9-001 to the Center for Innovative Minimally Invasive Therapy). The United States government may have certain rights in the invention."

with the following new section:

--This invention was made with Government support under Contract No. DAMD17-99-2-9001 awarded by the U.S. Army, under Grant No. EEC-9843342 awarded by the National Science Foundation, and under Grant No. R01 GM026698 awarded by the National Institutes of Health. The Government has certain rights in the invention.--

Signed and Sealed this
Sixteenth Day of February, 2016

Michelle K. Lee
*Director of the United States Patent and Trademark Office*